United States Patent
Kaplan et al.

(10) Patent No.: US 10,034,945 B2
(45) Date of Patent: Jul. 31, 2018

(54) SILK POWDER COMPACTION FOR PRODUCTION OF CONSTRUCTS WITH HIGH MECHANICAL STRENGTH AND STIFFNESS

(71) Applicant: TRUSTEES OF TUFTS COLLEGE, Medford, MA (US)

(72) Inventors: David L. Kaplan, Concord, MA (US); Fiorenzo Omenetto, Lexington, MA (US); Gary G. Leisk, Wilmington, MA (US); Tim Jia-Ching Lo, Taoyuan (TW); Benjamin Partlow, Marlborough, MA (US); Rosario Friedman, Conway, MA (US)

(73) Assignee: TRUSTEES OF TUFTS COLLEGE, Medford, MA (US)

( * ) Notice: Subject to any disclaimer, the term of this patent is extended or adjusted under 35 U.S.C. 154(b) by 0 days.

(21) Appl. No.: 14/414,245

(22) PCT Filed: Jul. 15, 2013

(86) PCT No.: PCT/US2013/050520
§ 371 (c)(1),
(2) Date: Jan. 12, 2015

(87) PCT Pub. No.: WO2014/012101
PCT Pub. Date: Jan. 16, 2014

(65) Prior Publication Data
US 2015/0174256 A1 Jun. 25, 2015

Related U.S. Application Data

(60) Provisional application No. 61/671,375, filed on Jul. 13, 2012.

(51) Int. Cl.
| | | |
|---|---|---|
| A61K 47/42 | (2017.01) | |
| B30B 9/28 | (2006.01) | |
| A61L 31/04 | (2006.01) | |
| A43B 1/02 | (2006.01) | |
| A43B 1/06 | (2006.01) | |
| A43B 13/02 | (2006.01) | |
| A43B 23/02 | (2006.01) | |
| A61L 27/36 | (2006.01) | |
| A61L 27/50 | (2006.01) | |

(52) U.S. Cl.
CPC ............ *A61K 47/42* (2013.01); *A43B 1/02* (2013.01); *A43B 1/06* (2013.01); *A43B 13/02* (2013.01); *A43B 23/0205* (2013.01); *A43B 23/0225* (2013.01); *A61L 27/3604* (2013.01); *A61L 27/50* (2013.01); *A61L 31/047* (2013.01); *B30B 9/28* (2013.01); *Y10T 29/49* (2015.01)

(58) Field of Classification Search
None
See application file for complete search history.

(56) References Cited

U.S. PATENT DOCUMENTS

| | | |
|---|---|---|
| 4,806,355 A | 2/1989 | Goosen et al. |
| 5,013,649 A | 5/1991 | Wang et al. |
| 5,015,476 A | 5/1991 | Cochrum et al. |
| 5,093,489 A | 3/1992 | Diamantoglou |
| 5,106,748 A | 4/1992 | Wozney et al. |
| 5,108,922 A | 4/1992 | Wang et al. |
| 5,116,738 A | 5/1992 | Wang et al. |
| 5,141,905 A | 8/1992 | Rosen et al. |
| 5,187,076 A | 2/1993 | Wozney et al. |
| 5,245,012 A | 9/1993 | Lombari et al. |
| 5,263,992 A | 11/1993 | Guire |
| 5,270,419 A | 12/1993 | Domb |
| 5,576,881 A | 11/1996 | Doerr et al. |
| 5,635,372 A | 6/1997 | Celeste et al. |
| 5,902,800 A | 5/1999 | Green et al. |
| 5,932,462 A | 8/1999 | Harris et al. |
| 5,965,403 A | 10/1999 | Celeste et al. |
| 6,127,143 A | 10/2000 | Gunasekaran |
| 6,245,537 B1 | 6/2001 | Williams et al. |
| 6,267,776 B1 | 7/2001 | O'Connell |
| 6,302,848 B1 | 10/2001 | Larson et al. |
| 6,310,188 B1 | 10/2001 | Mukherjee |
| 6,325,810 B1 | 12/2001 | Hamilton et al. |
| 6,337,198 B1 | 1/2002 | Levene et al. |
| 6,372,244 B1 | 4/2002 | Antanavich et al. |
| 6,379,690 B2 | 4/2002 | Blanchard et al. |
| 6,395,734 B1 | 5/2002 | Tang et al. |
| 6,524,597 B2 | 2/2003 | Kashimoto |
| 6,719,985 B1 | 4/2004 | Tsubouchi et al. |
| 7,842,780 B2 | 11/2010 | Kaplan et al. |

(Continued)

FOREIGN PATENT DOCUMENTS

| | | | |
|---|---|---|---|
| JP | 03-211024 | * | 0/1993 |
| JP | 03211024 | * | 9/1991 |

(Continued)

OTHER PUBLICATIONS

Rajkhowa et al. "Reinforcing Silk Scaffolds with Silk Particles". Jun. 2010.*
Rajkhowa et al. "Molecular Weight and Secondary Structure Change in Eri Silk During Alkali Degumming and Powdering". Mar. 2009.*
Khan et al. "Physical Properties and dyability of silk fibers degummed with citric acid".*
U.S. Appl. No. 61/613,185, filed Mar. 20, 2012, Kaplan et al.
U.S. Appl. No. 61/621,209, filed Apr. 6, 2012, Kaplan et al.
U.S. Appl. No. 61/719,146, filed Oct. 26, 2012, Kaplan et al.

(Continued)

*Primary Examiner* — Robert A Wax
*Assistant Examiner* — Danah Al-Awadi
(74) *Attorney, Agent, or Firm* — Quarles & Brady LLP

(57) ABSTRACT

The present disclosure relates generally to compositions and methods for production of three-dimensional constructs with high mechanical strength and/or stiffness.

14 Claims, 4 Drawing Sheets

(56) References Cited

U.S. PATENT DOCUMENTS

| | | |
|---|---|---|
| 2010/0028451 A1 | 2/2010 | Kaplan et al. |
| 2010/0178304 A1 | 7/2010 | Wang et al. |
| 2010/0183535 A1 | 7/2010 | Goetz et al. |
| 2010/0279112 A1 | 11/2010 | Kaplan et al. |
| 2011/0046686 A1 | 2/2011 | Kaplan et al. |
| 2011/0171239 A1 | 7/2011 | Kaplan et al. |

FOREIGN PATENT DOCUMENTS

| | | |
|---|---|---|
| JP | H05-38728 A | 2/1993 |
| JP | H07-250688 A | 10/1995 |
| WO | WO-91/18098 A1 | 11/1991 |
| WO | WO-93/00432 A1 | 1/1993 |
| WO | WO-93/09229 A1 | 5/1993 |
| WO | WO-93/16099 A2 | 8/1993 |
| WO | WO-94/01557 A1 | 1/1994 |
| WO | WO-94/05800 A1 | 3/1994 |
| WO | WO-94/15949 A1 | 7/1994 |
| WO | WO-94/15965 A1 | 7/1994 |
| WO | WO-94/15966 A1 | 7/1994 |
| WO | WO-94/21681 A1 | 9/1994 |
| WO | WO-94/26892 A1 | 11/1994 |
| WO | WO-94/26893 A1 | 11/1994 |
| WO | WO-95/01801 A1 | 1/1995 |
| WO | WO-95/01802 A1 | 1/1995 |
| WO | WO-95/07982 A1 | 3/1995 |
| WO | WO-95/10539 A1 | 4/1995 |
| WO | WO-95/16035 A2 | 6/1995 |
| WO | WO-95/18856 A1 | 7/1995 |
| WO | WO-96/01845 A1 | 1/1996 |
| WO | WO-96/02559 A1 | 2/1996 |
| WO | WO-96/16668 A1 | 6/1996 |
| WO | WO-96/17924 A2 | 6/1996 |
| WO | WO-97/08315 A1 | 3/1997 |
| WO | WO-2004/000255 A1 | 12/2003 |
| WO | WO-2004/000915 A2 | 12/2003 |
| WO | WO-2004/062697 A2 | 7/2004 |
| WO | WO-2005/012606 A2 | 2/2005 |
| WO | WO-2007/098951 A2 | 9/2007 |
| WO | WO-2008/118133 A2 | 10/2008 |
| WO | WO-2008/150861 A1 | 12/2008 |
| WO | WO-2009/023615 A1 | 2/2009 |
| WO | WO-2009/126689 A2 | 10/2009 |
| WO | WO-2011/005381 A2 | 1/2011 |
| WO | WO-2011/041395 A2 | 4/2011 |
| WO | WO-2013/142119 A1 | 9/2013 |
| WO | WO-2013/152265 A1 | 10/2013 |
| WO | WO-2014/012101 A1 | 1/2014 |

OTHER PUBLICATIONS

Acharya, C. et al., Performance evaluation of a silk protein-based matrix for the enzymatic conversion of tyrosine to L-DOPA, 3:226-233 (2008).

Bayraktar, O. et al., Silk fibroin as a novel coating material for controlled release of theophylline, Eur. J. Pharm. Biopharm, 60:373-381 (2005).

Demura, M. and Asakura, T., Immobilization of glucose oxidase with Bombyx mori silk fibroin by only stretching treatment and its application to glucose sensor, Biotechnol. Bioeng., 33(5):598-603 (1989).

Fukui, A. et al., Isolation and Characterization of *Xenopus* Follistatin and Activins, Devel. Biol., 159:131-139 (1993).

Hofmann, S., et al., Silk fibroin as an organic polymer for controlled drug delivery, Journal of Controlled Release, 111:219-227 (2006).

Hu, X. et al., Regulation of silk material structure by temperature-controlled water vapor annealing, Biomacromolecules, 12(5):1686-1696 (2011).

International Search Report for PCT/US2013/050520, 4 pages (dated Sep. 25, 2013).

Jin, H.J. et al., Water-Stable Silk Films with Reduced Beta-Sheet Content, Advanced Functional Materials, 15(8):1241-1247 (2005).

Jones et al., Isolation of *VGR*-2, a Novel Member of the Transforming Growth Factor-*beta*- Related Gene Family, Mol. Endocrinol., 611961 (1992).

Li, M. et al., Study on Porous Silk Fibroin Materials. II. Preparation and Characteristics of Spongy Porous Silk Fibroin Materials, J. Applied Polymer Science, 79:2192-2199 (2001).

Lovett, M. et al., Gel spinning of silk tubes for tissue engineering, Biomaterials, 29(35):4650-4657 (2008).

Lu, S. et al., Stabilization of Enzymes in Silk Films, Biomacromolecules, 10:1032-1042 (2009).

Lucas, F. et al., The silk fibroins, Adv. Protein. Chem., 13:107-242 (1958).

Mandal, B. et al., High-strength silk protein scaffolds for bone repair, Proceedings of the National Academy of Sciences USA, 109(20):7699-7704 (2012).

Min, S. et al., Preparation and Characterization of Crosslinked Porous Silk Fibroin Gel, Sen'l Gakkaishi, 54(2):85-92 (1997).

Miyairi, S. and Sugiura, M., Properties of beta-Glucosidase Immobilized in Sericin Membrane, J. Ferment. Technol., 56(4):303-308 (1978).

Nazarov, R. et al., Porous 3-D scaffolds from regenerated silk fibroin, Biomacromolecules, 5(3):718-26 (2004).

Sasai, Y. et al., Xenopus chordin: a novel dorsalizing factor activated by organizer-specific homeobox genes, Cell, 79(5):779-90 (1994).

Vepari, C. and Kaplan, D.L., Silk as a Biomaterial, Prog. Polym. Sci., 32(8-9):991-1007 (2007).

Wang, Y. et al., A Large Family of Putative Transmembrane Receptors Homologous to the Product of the Drosophila Tissue Polarity Gene frizzled, The Journal of Biological Chemistry, 271(8):4468-76 (1996).

Wenk, E. et al., Silk fibroin spheres as a platform for controlled drug delivery, J. Control. Release, 24;132(1):26-34 (2008).

Wray, L.S. et al., Effect of Processing on silk based biomaterials:Reproducibility and biocornpatibility, J. Biomedical Material Research Part B, 99B: 89-101 (2011).

Written Opinion for PCT/US2013/050520, 6 pages (dated Sep. 25, 2013).

Soong, H. K. and Kenyon, K. R., Adverse Reactions to Virgin Silk Sutures in Cataract Surgery, Ophthamology, 91(5): 479-483 (1984).

* cited by examiner i.  Freeze a silk solution and lyophilize;
ii. Break up lyophilized silk into small pieces and press them into the mold;
iii. Add HFIP, cover and let set;
iv. Submerge mold with dissolved silk in methanol, then slowly replace methanol with water;
v.  Remove blocks from mold and allow to dry;
vi. Machine blocks into final shapes.

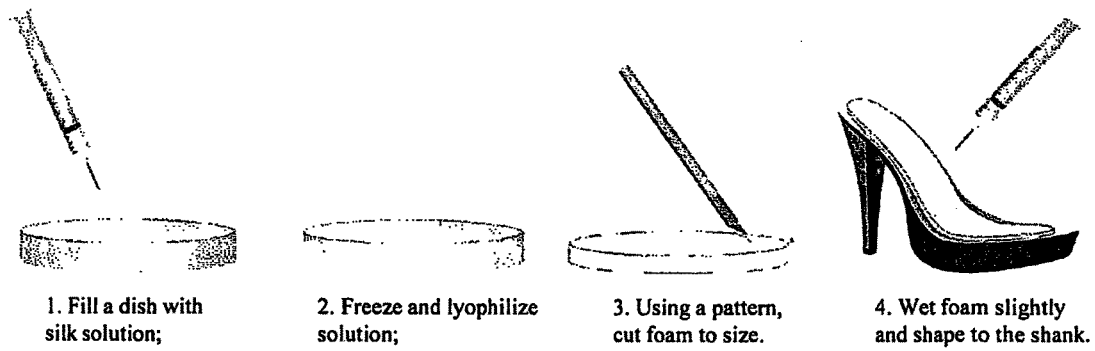

1. Fill a dish with silk solution;
2. Freeze and lyophilize solution;
3. Using a pattern, cut foam to size.
4. Wet foam slightly and shape to the shank.

FIG. 5

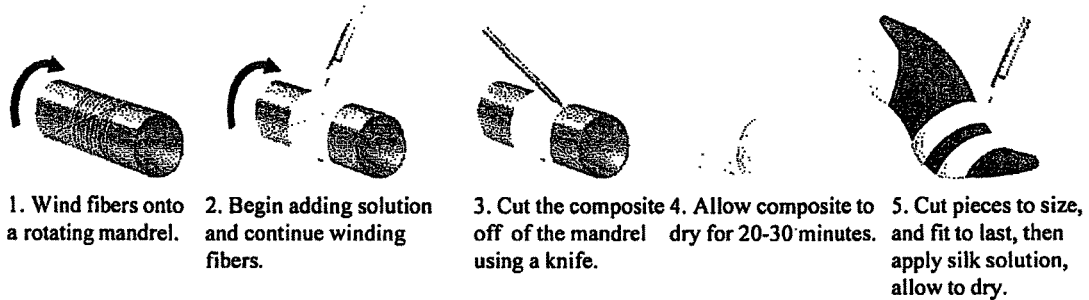

1. Wind fibers onto a rotating mandrel.
2. Begin adding solution and continue winding fibers.
3. Cut the composite off of the mandrel using a knife.
4. Allow composite to dry for 20-30 minutes.
5. Cut pieces to size, and fit to last, then apply silk solution, allow to dry.

SILK POWDER COMPACTION FOR PRODUCTION OF CONSTRUCTS WITH HIGH MECHANICAL STRENGTH AND STIFFNESS

RELATED APPLICATIONS

This application claims benefit under 35 U.S.C. § 119(e) of the U.S. Provisional Application No. 61/671,375, filed Jul. 13, 2012, the content of which is incorporated herein by reference in its entirety.

GOVERNMENT SUPPORT

This invention was made with government support under grant no. P41 EB002520 awarded by the National Institutes of Health. The government has certain rights in the invention.

TECHNICAL FIELD

The present disclosure relates generally to compositions and methods for production of three-dimensional constructs with high mechanical strength and/or stiffness.

BACKGROUND

Silk material is produced by thousands of species of spiders and by worms from various insects such as mites, butterflies, and moths. Silks produced by silkworms (typically *Bombyx Mori*) and orb-weaving spiders are widely studied due to their impressive mechanical properties, environmental stability, biocompatibility, and tunable degradation. In addition, such silk can be modified to deliver antibiotics, drugs, and growth factors to enhance healing in biomedical applications. Biomedical applications have seen successful introduction of silks, dating to the first usage of silk sutures centuries ago. See, for example, Vepari, C. and Kaplan, D. L., "Silk as a Biomaterial," Prog. Polym. Sci. 32 (2007), pp. 991-1007. However, there is no existing technologies that enable production of three-dimensional silk-based constructs with high mechanical strength and/or stiffness.

SUMMARY

Compositions and methods describe herein relate to fabrication of robust silk material formats using a novel powder compaction technique. In some embodiments, the process is shown to generate a variety of construct geometries with greatly enhanced mechanical performance over existing regenerated silk materials. The silk-based materials described herein range from monolithic materials (e.g., silk powder bound and fused together under elevated temperature and pressure) to composite materials (e.g., silk-silk composites made from silk "matrix" and silk reinforcing phases combined into one consolidated material or part). The fabrication techniques described herein can be extended to other protein or non-protein based materials.

BRIEF DESCRIPTION OF THE DRAWINGS

FIGS. 3-5 are schematic representations of a method for preparing parts of the 100% silk shoe.

DETAILED DESCRIPTION OF EXEMPLARY EMBODIMENTS

Figure 1A:
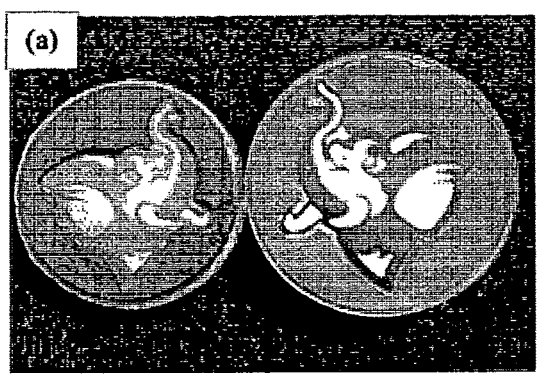
FIGS. 1A and 1B are photographs of silk construct made using high-resolution acrylic die insert: the construct (left) and acrylic die insert (FIG. 1A) and stereomicroscope image of fine detail on silk construct (FIG. 1B).

While the fiber form of silk is used in suture or textile-based applications, a solubilized form of silk fibroin is effective and versatile in creating unique three-dimensional morphologies and materials for applications that range beyond the traditional textile-based applications. In a typical protocol, 5 grams of *B. mori* silkworm cocoons are immersed in 1 L of boiling 0.02 M $Na_2CO_3$ solution for 30 minutes. This degumming process removes a protein known as sericin, which coats the silk fibroin and acts as a glue-like substance. Degummed fibers are collected and rinsed with distilled water three times, then air-dried. The fibers are then solubilized in 9.3 M LiBr (20% w/v) at 60° C. for 4 hours. A volume of 15 mL of this solution is then dialyzed against 1 L of distilled water (water changes after 1, 3, 6, 24, 36, and 48 hours) with a regenerated cellulose membrane (3500 MWCO, Slide-A-Lyzer, Pierce, Rockford, Ill.). The solubilized silk protein solution is then centrifuged twice (9700 RPM, 20 min., 4° C.) to remove insoluble particulates. Protein concentration is then determined by drying a known volume of the silk solution under a hood for 12 hours and assessing the mass of the remaining solids. See, for example, Wray, L. S., Hu, X., Gallego, J., Georgakoudi, I., Omenetto, F. G., Schmidt, D. and Kaplan, D. L., "Effect of Processing on Silk-Based Biomaterials: Reproducibility and Biocompatibility," Journal of Biomedical Materials Research Part B: Applied Biomaterials 99B: 1 (2001), pp. 89-10, content of which is incorporated herein by reference in its entirety.

Solubilized silk (also referred to as silk solution herein) can be processed to create a range of material formats, such as films, foams, fibers, gels, and sponges. Typically, these materials and/or material forms exhibit soft or flexible material response (e.g., low hardness, low tensile/compressive strength, and low flexural stiffness). While these responses have not restricted the usage of silk in implantation or repair applications involving soft tissues, there is a need to explore the creation of silk materials and scaffolds that have much better mechanical performance. For example, silk-based tissue engineering constructs are being proposed for bone repair or replacement. For this application, excellent strength and toughness properties are requisite to provide structural support within the body.

Accordingly, in one aspect, the disclosure provides a method for preparing an article of manufacture. Generally, the method comprises compacting or consolidating a silk composition. The silk in the composition can be in an at least partially insoluble state. After compaction, the composition can be in a solid state. After compaction, the composition can optionally be processed into a desired final shape.

In some embodiments, the silk fibroin composition is in form of a powder, i.e., the composition comprises silk particles. The silk particles can be nanoparticles or microparticles. As used herein, the term "particle" includes spheres; rods; shells; and prisms; and these particles can be part of a network or an aggregate. Without limitations, the particle can have any size from nm to millimeters. In some embodiments, the particles can have a size ranging from about 0.01 μm to about 1000 μm, about 0.05 μm to about 500

µm, about 0.1 µm to about 250 µm, about 0.25 µm to about 200 µm, or about 0.5 µm to about 100 µm. Further, the silk particle can be of any shape or form, e.g., spherical, rod, elliptical, cylindrical, capsule, or disc. In some embodiments, the silk particle is a microparticle or a nanoparticle. As used herein, the term "microparticle" refers to a particle having a particle size of about 1 µm to about 1000 µm. As used herein, the term "nanoparticle" refers to particle having a particle size of about 0.1 nm to about 1000 nm.

Without wishing to be bound by a theory, particle size can greatly determine microscopic and macroscopic properties of the final product. Particle size is dependent on a number of process parameters, including, but not limited to, the size of the ceramic balls used, the amount of silk placed in each ball mill cup, the rotational speed (RPM) of the machine, and the duration of ball milling. Particle size in the powder can be predicted based on some of these process parameters, e.g., with mathematical modeling and/or experimentation to determine the correlation. For example, this can be done by milling a given volume of silk fibroin for varying ball mill speeds and durations. Scanning Electron Microscopy (SEM) can be performed on representative samples from each experiment to determine particle size. Additional tests can be run on each sample to determine the effect of process parameters on the color, molecular weight, viscosity in a solution, and solubility in water of the resulting constructs.

In some embodiments, the silk particles comprise silk fibroin substantially free of sericin. In some embodiments, the silk particles comprise non-degummed silk or partially degummed silk (i.e., silk having some amount of sericin). Silk fibers are composed of fibroin and sericin proteins. For biomedical applications, the sericin can be removed before implantation to prevent immunogenic responses. This can be done through a process known as degumming. For example, 5 grams of *B. mori* silkworm cocoons can be immersed in 1 L of boiling 0.02 M $Na_2CO_3$ solution for 30 minutes. Degummed fibers can be collected and rinsed with distilled water (e.g., three times) and air-dried. A calibrated inspection tool can be developed to measure sericin. In some embodiments, a tunable amount of sericin can be left in the silk material after degumming. This can eliminate the need to mix together silk particles prepared from degummed and non-degummed silk fibroin.

Silk powder can be useful in many applications, for example, as a filler in silk gels or other silk forms or possibly as a crystallite-like material to enhance (acting as a catalyst) conversion of a silk solution into a hydrogel. For the hard silk material described in the present process, in some embodiments, a liquid binder can be added to the silk particle composition. Taking advantage of the ability of sericin protein to act as a glue-like binder in silkworm cocoons, in some embodiments, the method disclosed herein comprises mixing in a combination of silk particles made from degummed and silk particles made from non-degummed silk fibroin. To control the amount of sericin, a specific proportion of each can be weighed and mixed together. The particles are mixed together vigorously to ensure that the final mixture is homogeneous.

The mixture can comprise from 100% non-degummed silk to 100% degummed silk. Without wishing to be bound by theory, the consolidation ability, level of bonding, and strength properties of the final construct can be likely highly dependent on the sericin content. Another variation that can occur in this step includes the addition of other silk (and non-silk) materials to reinforce the construct. Various composite architectures can be used, for example, from chopped or continuous fiber reinforcement, to the embedding of textile-like reinforcing layers. In addition to mechanical reinforcing phases, there are many art-recognized additives that can be used, each of which can affect the final product differently.

In some embodiments, the composition comprises a mixture of silk particles comprising degummed silk and silk particles comprising non-degummed silk. Ratio of degummed silk to non-degummed silk in the composition can range from about 50:1 (w/w) to about 1:50 (w/w). In some embodiments, ratio of degummed silk to non-degummed silk in the composition can range from about 25:1 (w/w) to about 1:25 (w/w), from about 20:1 (w/w) to about 1:20 (w/w), from about 15:1 (w/w) to about 1:15 (w/w), from about 10:1 (w/w) to about 1:10 (w/w), from about 5:1 (w/w) to about 1:25 (w/w), from about 1:1 (w/w) to about 1:20, from about 1:1 (w/w) to about 1:15 (w/w), or from about 1:2.5 (w/w) to about 1:10 (w/w).

Various methods of producing silk particles (e.g., nanoparticles and microparticles) are known in the art. For example, a milling machine (e.g., a Retsch planetary ball mill) can be used to produce silk powder. Generally, the ball mill consists of either two or four sample cups arranged around a central axis, which is geared such that each cup rotates both centrally and locally. Each ceramic cup is filled with small ceramic spheres. A range of sizes is available; balls with a diameter of 10 millimeters were/are used for the milling operations described in the present disclosure. As the cups spin, the spheres crush material in the cups to a small characteristic size. Both degummed and non-degummed silk can be converted from pulverized material to powder form in the ball mill.

Before milling, a pulverization step can be used to break up silk fibroin in the form of whole cocoons or bave silk before introduction to a ball mill. If the cocoons are not shredded, it is possible that the ball mill can take a significant amount of time to crush the cocoons into powder. One issue, however, can be related to the degradation (decreased molecular weight of silk fibroin) from pulverization. Testing with SDS-PAGE (gel electrophoresis) has shown that pulverizing silk before degumming can degrade molecular weight significantly, when compared to silk that was not pulverized. While this can have a negative impact on the final properties achievable in the silk constructs, elimination of this step may not provide a significant benefit. Without wishing to be bound by theory, the ball milling operation can degrade the silk material as well. In some embodiments, the milling can be used to produce powders. In other embodiments, alternative powder formation techniques can be used (e.g., lyophilization or flash freezing and crushing). In other embodiments, alternative grates on the pulverizer, with larger holes, can be used. This can generate larger silk particle sizes.

Generally, for pulverization, dried silk is placed into a pulverizer, e.g., Fritsch Pulverisette 19, which "pulverizes" the silk by forcing it through a grate by the rotating action of a 5-bladed milling cutter. To ensure proper flow of the silk material through the pulverizer (e.g., Pulverisette), a vacuum (e.g., an industrial vacuum) can be attached to the outflow tube on the bottom of the grate. Pulverized silk can then be collected from the inside of the industrial vacuum. Generally, the resulting silk material is chopped and fluffy, made up of fairly short silk particles. Given the availability of additional grates with unique perforation size, silk particles of varying length can be produced.

In some embodiments, the silk particles can be produced by a polyvinyl alcohol (PVA) phase separation method as described in, e.g., International App. No. WO 2011/041395, the content of which is incorporated herein by reference in its entirety. Other methods for producing silk fibroin particles are described, for example, in U.S. App. Pub. No. U.S. 2010/0028451 and PCT App. Pub. No.: WO 2008/118133 (using lipid as a template for making silk microspheres or nanospheres), and in Wenk et al. J Control Release, Silk fibroin spheres as a platform for controlled drug delivery, 2008; 132: 26-34 (using spraying method to produce silk microspheres or nanospheres), content of all of which is incorporated herein by reference in its entirety.

In some embodiments, silk particles can be produced using a freeze-drying method as described in U.S. Provisional Application Ser. No. 61/719,146, filed Oct. 26, 2012, content of which is incorporated herein by reference in its entirety. Specifically, silk foam can be produced by freeze-drying a silk solution. The foam then can be reduced to particles. For example, a silk solution can be cooled to a temperature at which the liquid carrier transforms into a plurality of solid crystals or particles and removing at least some of the plurality of solid crystals or particles to leave a porous silk material (e.g., silk foam). After cooling, liquid carrier can be removed, at least partially, by sublimation, evaporation, and/or lyophilization. In some embodiments, the liquid carrier can be removed under reduced pressure. After formation, the silk fibroin foam can be subjected to grinding, cutting, crushing, or any combinations thereof to form silk particles. For example, the silk fibroin foam can be blended in a conventional blender or milled in a ball mill to form silk particles of desired size.

The term "compacting" can be understood to mean reduce in volume and/or increase in density. One way of compacting the silk fibroin composition can be by applying pressure to the composition. Accordingly, in some embodiments, the method comprises providing a silk composition, wherein the silk fibroin can be in an at least partially insoluble state; and applying pressure to the composition.

The pressure can be applied using a press, e.g., designed specifically for this purpose. In one non-limiting example, the press is composed of 4 parts—a base plate, a cavity plate, a top plate, and a piston. The base plate is attached to the cavity plate by four ¼"-20 bolts to form a well. The silk composition is deposited in the well, and the piston is inserted into position. The piston is machined to just fit inside the well to minimize the amount the composition that can leak out upon compaction. Next the top plate is bolted onto the cavity plate, and the bolts are tightened using a torque wrench such that there is a specific amount of pressure on the material inside the press. It is important for the pressure to be sufficient and for the consistency of the compound to be correct, otherwise the compound can leak, or the resulting material can be inconsistent and non-homogenous.

Applying adequate pressure is desirable during the compaction process. With insufficient pressure, the final construct can be porous and easily crack. With over-pressure, as with the addition of too much binder, e.g., water, the compound can leak out of the press, generating a final construct with poor geometric stability and poor mechanical performance. Accordingly, in some embodiments, an integrated, one-piece bottom plate/cavity plate can be developed. This can prevent leakage at the base of the well. However, removal of the final construct can become more difficult. Alternatively, the well and piston can be fabricated with draft angles, which can allow for easier construct removal.

The pressure to be applied to the composition can be a pressure of about 0.05 bar, about 0.1 bar, about 0.15 bar, about 0.2 bar, about 0.25 bar, about 0.3 bar, about 0.35 bar, about 0.4 bar, about 0.45 bar, about 0.5 bar, about 0.55 bar, about 0.6 bar, about 0.65 bar, about 0.7 bar, about 0.75 bar or higher. For example, the pressure can be about 1 bar, 1.25 bar, 1.5 bar, 1.75 bar, 2 bar, 2.25 bar, 2.5 bar, 2.75 bar, 3 bar, 3.25 bar, 3.5 bar, 3.75 bar, 4 bar, 4.25 bar, 4.5 bar, 4.75 bar, 5 bar, 5.25 bar, 5.5 bar, 5.75 bar, 6 bar, 7.25 bar, 7.5 bar, 7.75 bar, 8 bar, 8.25 bar, 8.5 bar, 8.75 bar, 9 bar, 9.25 bar, 9.5 bar, 9.75 bar, 10 bar, or higher. In some embodiments, the pressure is about 1 bar or higher.

It is to be noted, that the method disclosed herein differs from the methods wherein the composition is incubated under pressure but a pressure is not directly applied to the composition. In the method disclosed herein, the silk fibroin composition is compacted by applying a pressure directly to the composition.

As used herein the term "insoluble state" when used in reference to a silk fibroin refers to the formation of or state of being in a substantially amorphous, primarily beta-sheet conformation. The term "formed into an insoluble state" is not intended to reflect polymerization of silk monomers into a silk polymer. Rather, it is intended to reflect the conversion of soluble silk fibroin to a water insoluble state. As used herein, silk fibroin is in an "insoluble state" if it can be pelleted by centrifugation or if it cannot be dissolved by immersion in or rinsing with water at 37° C. or less.

Without limitation, compaction can be carried out at any desired temperature. In some embodiments, compaction is at room temperature. In some other embodiments, compaction is at an elevated temperature. As used herein, the term "elevated temperature" means a temperature higher that room temperature. Generally, the elevated temperature is a temperature higher than about 25° C. For example, the elevated temperature can be temperature of about 30° C. or higher, about 35° C. or higher, about 40° C. or higher, about 45° C. or higher, about 50° C. or higher, about 55° C. or higher, about 60° C. or higher, about 65° C. or higher, about 70° C. or higher, about 75° C. or higher, about 80° C. or higher, about 85° C. or higher, about 90° C. or higher, about 95° C. or higher, about 100° C. or higher, about 105° C. or higher, about 110° C. or higher, about 115° C. or higher, about 120° C. or higher, about 125° C. or higher, about 130° C. or higher, about 135° C. or higher, about 140° C. or higher, about 145° C. or higher, or about 150° C. or higher. In some embodiments, compaction can be at room temperature, about 60° C., or about 120° C.

In some embodiments, with the composition under pressure in a compaction press, the entire press can be placed in a preheated oven for a specific amount of time.

Without wishing to be bound by a theory, mechanistically, the consolidation process that occurs with the silk powder is likely related to the glass transition temperature (Tg) of the polymer involved. While it is widely reported that the Tg for silk fibroin is in the range of 190° C. to 210° C., the Tg can shift depending on molecular weight. Given the degradation that occurs due to the pulverizing and ball milling operations, the silk powder generated likely has a much lower Tg. The Tg of silk before and after pulverizing and ball milling can be determined using analytical techniques, such as Differential Scanning calorimetry (DSC). The temperature used during the consolidation process can affect the mechanical property of the final construct. If the temperature is too high or the material is left in the oven too long, sample burning can occur. If the temperature is too low or the material is not maintained at elevated temperature long enough, the sample could be soft and not fully dry, leading to construct deformation, inhomogeneity, and poor mechanical robustness.

Without limitation, compaction can be for any desired period of time. For example, the compaction can be for a period of minutes, hours, or days. For example, the compaction can be for a period of about one hour, two hours, three hours, four hours, five hours, six hours, twelve hours, one day, two days, three days or longer.

The compaction time and/or temperature can affect the sample greatly. For example, if the temperature is too low or the heating time too short, the sample typically does not consolidate well (not cooked through). If the temperature is too high or the heating time too long, the sample appears to overheat and even burn (over-cooking). In either case, the resulting construct can have poor geometric stability and limited mechanical robustness.

If the compaction is at an elevated temperature, it can be desirable to cool the compacted composition before removal from removing it from the press. Cooling (e.g., complete cooling) can be desirable before removal of the compacted composition from the press or the compacted composition can warp as it cools outside of the press. The compacted composition can be cooled for any desired period of time before removal from the press. In some embodiments, the press can be removed from the oven and placed in a fume hood to cool by convection with room temperature air. Once completely cool, the bolts can be released and the sample removed.

In some embodiments, the silk composition can further comprise a binder. As used herein, the term "binder" includes any additive which imparts cohesive qualities and is used for the purpose of binding or holding together powdered components in a solid compacted form. Suitable binders depend on the individual application and are known to, and can be determined by, the person skilled in the art. Without wishing to be bound by theory, hydration of the sericin and possibly fibroin can cause the material to become slightly sticky; e.g., recapitulating the glue-like response of sericin naturally produced by silkworms.

In some embodiments, the binders contemplated are liquids, e.g., water, salt solutions, and the like. Amount of liquid binder in the silk composition can range from about 0.1% (w/w) to about 75% (w/w) of the total of the composition. In some embodiments, amount of the liquid binder in the silk composition can range from about 5% (w/w) to about 65% (w/w) from about 10% (w/w) to about 60% (w/w), from about 15% (w/w) to about 50% (w/w), from about 20% (w/w) to about 45% (w/w), or from about 25% (w/w) to about 40% (w/w). In some embodiments, it is can be desirable to use a ratio of 3 to 6 grams of silk particles for every 2 ml of liquid binder. Generally, the amount of the liquid binder in the composition is sufficient to provide a silk composition of a desired viscosity.

In some embodiments, the binder is a solubilized silk solution. Given the ability to easily adjust concentration (silk fibroin-to-water ratio), this provides additional flexibility for preparing the silk composition comprising the binder. Silk solution can act as a good binder for other forms of silk. There can be a number of potential benefits, beyond improved mechanical performance. The concentration, viscosity, molecular weight, and conformational makeup of the silk fibroin/water solution likely can have effects on the consistency and properties of the material during the process and the final constructs.

The consistency of the liquid binder comprising composition needs to be correct. With an insufficient quantity of liquid binder, the compacted composition can likely become inhomogeneous and possibly develop cracks and exhibit poor mechanical properties. With too much binder, the composition viscosity can likely become too low and prevent proper consolidation in the press (leakage from under the piston and likely development of voids or geometrical unstable constructs.

In some embodiments, the silk composition has a paste (or paste-like) consistency. In some embodiments, paste (or paste-like) consistency means that the composition is malleable or moldable. Paste consistency can be stated in terms of the viscosity of the solution. In some embodiments, viscosity of the composition can range from about 0.1 to about 250 Pa·s, from about 0.2 to about 150 Pa·s, from about 0.3 to about 100 Pa·s, from about 0.4 to about 50 Pa·s, or from about 0.5 to about 25 Pa·s. Compositions with overly high viscosity can be difficult to spread, smooth, and shape, while those with excessively low viscosity can be difficult to handle for molding purposes. Without wishing to be bound by a theory, compositions of higher viscosity can be used without a mold. For example, a composition of higher viscosity can be formed into a simple geometric shape by mechanical means, e.g. hands. Compositions of lower viscosity can be used for injection molding into molds of predetermined shape or into molds of simple geometric shapes. Compositions of higher viscosity can also be used for injection molding into predetermined shapes or simple geometric shapes.

Viscosity can be measured with various types of viscometers and rheometers. A rheometer is generally used for those fluids which cannot be defined by a single value of viscosity and therefore require more parameters to be set and measured than is the case for a viscometer. In some embodiments, viscosity can be determined at room temperature.

In some embodiments, a small amount of distilled water is measured and added to the silk composition comprising silk particles, e.g., with a 1 ml syringe. For example, a few drops of water can be added at a time and mixed with the silk particles. Once all water is added, a thorough mixing yields a viscous and sticky compound that has the consistency of smooth peanut butter.

In some embodiments, the compacted composition is a hard material, with a ceramic-like feel. Mechanical response varies widely depending on the parameters selected throughout the process.

After compaction, the compacted composition can be processed into the final desired shape to obtain an article of manufacture. As used herein, the term "processing" with reference to processing into the desired shape should be understood to include any method or process used to provide the final shape of the manufactured article. Without limitation, such processing can include, but is not limited to, mechanical and chemical means. For example, processing can be selected from the group consisting of machining, turning (lathe), rolling, thread rolling, drilling, milling, sanding, punching, die cutting, blanking, broaching, extruding, chemical etching, and any combinations thereof. As used herein, the term "machining" should be understood to include all types of machining operations including, but not limited to, CNC machining, cutting, milling, turning, drilling, shaping, planing, broaching, sawing, burnishing, grinding, and the like. One or more of the processing methods can be used in combination to obtain more complex, intricate geometries. The term "machinable" means a material which can be readily subjected to machining.

Accordingly, in some embodiments, the method comprises: (i) providing a composition comprising silk particles;

(ii) compacting the composition by application of pressure; and (iii) processing the compacted composition to a desired shape.

In some embodiments, the composition is in a mold. As used herein, the term "mold" is intended to encompass any mold, container or substrate capable of shaping, holding or supporting the silk composition. Thus, the mold in its simplest form could simply comprise a supporting surface. The mold can be of any desired shape, and can be fabricated from any suitable material including polymers (such as polysulphone, polypropylene, polyethylene), metals (such as stainless steel, titanium, cobalt chrome), ceramics (such as alumina, zirconia), glass ceramics, and glasses (such as borosilicate glass). In some embodiments, the mold can provide a scaffold of simple geometry, which can be processed into the final desired shape, i.e., the mold can be used to provide a blank which can be processed to the final shape.

As used herein, the term "silk fibroin" or "fibroin" includes silkworm fibroin and insect or spider silk protein. See e.g., Lucas et al., 13 Adv. Protein Chem. 107 (1958). Any type of silk fibroin can be used according to aspects of the present invention. Silk fibroin produced by silkworms, such as *Bombyx mori*, is the most common and represents an earth-friendly, renewable resource. For instance, silk fibroin used in can be attained by extracting sericin from the cocoons of *B. mori*. Organic silkworm cocoons are also commercially available. There are many different silks, however, including spider silk (e.g., obtained from *Nephila clavipes*), transgenic silks, genetically engineered silks (recombinant silk), such as silks from bacteria, yeast, mammalian cells, transgenic animals, or transgenic plants, and variants thereof, that can be used. See for example, WO 97/08315 and U.S. Pat. No. 5,245,012, content of both of which is incorporated herein by reference in its entirety. In some embodiments, silk fibroin can be derived from other sources such as spiders, other silkworms, bees, and bioengineered variants thereof. In some embodiments, silk fibroin can be extracted from a gland of silkworm or transgenic silkworms. See for example, WO2007/098951, content of which is incorporated herein by reference in its entirety. In some embodiments, silk fibroin is free, or essentially free of sericin, i.e., silk fibroin is a substantially sericin-depleted silk fibroin.

Degummed silk can be prepared by any conventional method known to one skilled in the art. For example, *B. mori* cocoons are boiled for about up to 60 minutes, generally about 30 minutes, in an aqueous solution. In one embodiment, the aqueous solution is about 0.02M $Na_2CO_3$. The cocoons are rinsed, for example, with water to extract the sericin proteins. The degummed silk can be dried and used for preparing silk powder. Alternatively, the extracted silk can dissolved in an aqueous salt solution. Salts useful for this purpose include lithium bromide, lithium thiocyanate, calcium nitrate or other chemicals capable of solubilizing silk. In some embodiments, the extracted silk can dissolved in about 8M-12 M LiBr solution. The salt is consequently removed using, for example, dialysis.

If necessary, the solution can then be concentrated using, for example, dialysis against a hygroscopic polymer, for example, PEG, a polyethylene oxide, amylose or sericin. In some embodiments, the PEG is of a molecular weight of 8,000-10,000 g/mol and has a concentration of about 10% to about 50% (w/v). A slide-a-lyzer dialysis cassette (Pierce, MW CO 3500) can be used. However, any dialysis system can be used. The dialysis can be performed for a time period sufficient to result in a final concentration of aqueous silk solution between about 10% to about 30%. In most cases dialysis for 2-12 hours can be sufficient. See, for example, International Patent Application Publication No. WO 2005/012606, the content of which is incorporated herein by reference in its entirety.

The silk fibroin solution can be produced using organic solvents. Such methods have been described, for example, in Li, M., et al., J. *Appl. Poly Sci.* 2001, 79, 2192-2199; Min, S., et al. *Sen'I Gakkaishi* 1997, 54, 85-92; Nazarov, R. et al., *Biomacromolecules* 2004 May-June; 5(3):718-26, content of all which is incorporated herein by reference in their entirety. An exemplary organic solvent that can be used to produce a silk solution includes, but is not limited to, hexafluoroisopropanol (HFIP). See, for example, International Application No. WO2004/000915, content of which is incorporated herein by reference in its entirety. In some embodiments, the silk solution is free or essentially free of organic solvents, i.e., solvents other than water.

Generally, any amount of silk fibroin can be present in the solution. For example, amount of silk in the solution or the composition prepared therefrom can be from about 1% (w/v) to about 50% (w/v) of silk, e.g., silk fibroin. In some embodiments, the amount of silk in the solution or the composition prepared therefrom can be from about 1% (w/v) to about 35% (w/v), from about 1% (w/v) to about 30% (w/v), from about 1% (w/v) to about 25% (w/v), from about 1% (w/v) to about 20% (w/v), from about 1% (w/v) to about 15% (w/v), from about 1% (w/v) to about 10% (w/v), from about 5% (w/v) to about 25% (w/v), from about 5% (w/v) to about 20% (w/v), from about 5% (w/v) to about 15% (w/v). In some embodiments, the silk in the silk solution is about 25% (w/v). In some embodiments, the silk in the silk solution is about 6% (w/v) to about 8% (w/v). Exact amount of silk in the silk solution can be determined by drying a known amount of the silk solution and measuring the mass of the residue to calculate the solution concentration.

The silk fibroin can be used to fabricate a silk fibroin-based scaffold which can then be used to produce silk particles for use in the disclosed method. For example, the silk fibroin solution can be formed into silk fibroin-based scaffold such as a fiber, film, gel, hydrogel, foam, mesh, mat, or non-woven mat. The silk fibroin-based scaffold (e.g., fiber, film, gel, hydrogel, foam, mesh, mat, or non-woven mat) can be processed by subjecting the silk fibroin-based scaffold to milling, grinding, cutting, crushing, or any combinations thereof to form silk particles. For example, the silk fibroin-based scaffold can be blended in a conventional blender or milled in a ball mill to form silk particles of desired size.

The silk fibroin-based scaffold can be in any form, shape or size. Accordingly, in some embodiments, the silk fibroin-based material is in the form of a fiber. As used herein, the term "fiber" means a relatively flexible, unit of matter having a high ratio of length to width across its cross-sectional perpendicular to its length. Methods for preparing silk fibroin fibers are well known in the art. A fiber can be prepared by electrospinning a silk solution, drawing a silk solution, and the like. Electrospun silk materials, such as fibers, and methods for preparing the same are described, for example in WO2011/008842, content of which is incorporated herein by reference in its entirety. Micron-sized silk fibers (e.g., 10-600 μm in size) and methods for preparing the same are described, for example in Mandal et al., PNAS, 2012, doi: 10.1073/pnas.1119474109; U.S. Provisional Application No. 61/621,209, filed Apr. 6, 2012; and PCT application no. PCT/US13/35389, filed Apr. 5, 2013, content of all of which is incorporated herein by reference In some embodiments, the silk fibroin-based scaffold can be in the form of a film, e.g., a silk film. As used herein, the term "film" refers to a flat or tubular flexible structure. It is to be noted that the term "film" is used in a generic sense to include a web, film, sheet, laminate, or the like. In some embodiments, the film is a patterned film, e.g., nanopatterned film. Exemplary methods for preparing silk fibroin films are described in, for example, WO 2004/000915 and WO 2005/012606, content of both of which is incorporated herein by reference in its entirety.

In some embodiments, the silk fibroin-based scaffold can be in the form of a gel or hydrogel. The term "hydrogel" is used herein to mean a silk-based material which exhibits the ability to swell in water and to retain a significant portion of water within its structure without dissolution. Methods for preparing silk fibroin gels and hydrogels are well known in the art. Methods for preparing silk fibroin gels and hydrogels include, but are not limited to, sonication, vortexing, pH titration, exposure to electric field, solvent immersion, water annealing, water vapor annealing, and the like. Exemplary methods for preparing silk fibroin gels and hydrogels are described in, for example, WO 2005/012606, content of which is incorporated herein by reference in its entirety. In some embodiments, the silk fibroin-based scaffold can be in the form of a sponge or foam. Methods for preparing silk fibroin gels and hydrogels are well known in the art. In some embodiments, the foam or sponge is a patterned foam or sponge, e.g., nanopaterned foam or sponge. Exemplary methods for preparing silk foams and sponges are described in, for example, WO 2004/000915, WO 2004/000255, and WO 2005/012606, content of all of which is incorporated herein by reference in its entirety.

In some embodiments, the silk fibroin-based scaffold can be in the form of a cylindrical matrix, e.g., a silk tube. The silk tubes can be made using any method known in the art. For example, tubes can be made using molding, dipping, electrospinning, gel spinning, and the like. Gel spinning is described in Lovett et al. (Biomaterials, 29(35):4650-4657 (2008)) and the construction of gel-spun silk tubes is described in PCT application no. PCT/US2009/039870, filed Apr. 8, 2009, content of both of which is incorporated herein by reference in their entirety. Construction of silk tubes using the dip-coating method is described in PCT application no. PCT/US2008/072742, filed Aug. 11, 2008, content of which is incorporated herein by reference in its entirety. Construction of silk fibroin tubes using the film-spinning method is described in PCT application No. PCT/US2013/030206, filed Mar. 11, 2013 and U.S. Provisional application No. 61/613,185, filed Mar. 20, 2012.

In some embodiments, the silk fibroin-based scaffold can be porous. For example, the silk fibroin-matrix can have a porosity of at least about 10%, at least about 20%, at least about 30%, at least about 40%, at least about 50%, at least about 60%, at least about 70%, at least about 80%, at least about 90%, or higher. As used herein, the term "porosity" is a measure of void spaces in a material and is a fraction of volume of voids over the total volume, as a percentage between 0 and 100% (or between 0 and 1). Determination of porosity is well known to a skilled artisan, e.g., using standardized techniques, such as mercury porosimetry and gas adsorption, e.g., nitrogen adsorption.

The porous silk-based scaffold can have any pore size. As used herein, the term "pore size" refers to a diameter or an effective diameter of the cross-sections of the pores. The term "pore size" can also refer to an average diameter or an average effective diameter of the cross-sections of the pores, based on the measurements of a plurality of pores. The effective diameter of a cross-section that is not circular equals the diameter of a circular cross-section that has the same cross-sectional area as that of the non-circular cross-section.

Methods for forming pores in silk fibroin-based scaffolds are known in the art and include, but are not limited, porogen-leaching methods, freeze-drying methods, and/or gas-forming method. Exemplary methods for forming pores in a silk-based material are described, for example, in U.S. Pat. App. Pub. Nos.: US 2010/0279112 and US 2010/0279112; U.S. Pat. No. 7,842,780; and WO2004062697, content of all of which is incorporated herein by reference in its entirety.

Though not meant to be bound by a theory, silk fibroin-based scaffold's porosity, structure, and mechanical properties can be controlled via different post-spinning processes such as vapor annealing, heat treatment, alcohol treatment, air-drying, lyophilization and the like. Additionally, any desirable release rates, profiles or kinetics of a molecule encapsulated in the matrix can be controlled by varying processing parameters, such as matrix thickness, silk molecular weight, concentration of silk in the matrix, beta-sheet conformation structures, silk II beta-sheet crystallinity, or porosity and pore sizes.

In some embodiments, the method further comprises inducing a conformational change in silk fibroin to make the silk fibroin at least partially insoluble. Without wishing to be bound by a theory, the induced conformational change alters the crystallinity of the silk fibroin, e.g., Silk II beta-sheet crystanllinity. The conformational change can be induced by any methods known in the art, including, but not limited to, alcohol immersion (e.g., ethanol, methanol), water annealing, shear stress, ultrasound (e.g., by sonication), pH reduction (e.g., pH titration and/or exposure to an electric field) and any combinations thereof. For example, the conformational change can be induced by one or more methods, including but not limited to, controlled slow drying (Lu et al., 10 Biomacromolecules 1032 (2009)); water annealing (Jin et al., Water-Stable Silk Films with Reduced β-Sheet Content, 15 Adv. Funct. Mats. 1241 (2005); Hu et al. Regulation of Silk Material Structure by Temperature-Controlled Water Vapor Annealing, 12 Biomacromolecules 1686 (2011)); stretching (Demura & Asakura, Immobilization of glucose oxidase with *Bombyx mori* silk fibroin by only stretching treatment and its application to glucose sensor, 33 Biotech & Bioengin. 598 (1989)); compressing; solvent immersion, including methanol (Hofmann et al., Silk fibroin as an organic polymer for controlled drug delivery, 111 J Control Release. 219 (2006)), ethanol (Miyairi et al., Properties of b-glucosidase immobilized in sericin membrane. 56 J. Fermen. Tech. 303 (1978)), glutaraldehyde (Acharya et al., Performance evaluation of a silk protein-based matrix for the enzymatic conversion of tyrosine to L-DOPA. 3 Biotechnol J. 226 (2008)), and 1-ethyl-3-(3-dimethyl aminopropyl) carbodiimide (EDC) (Bayraktar et al., Silk fibroin as a novel coating material for controlled release of theophylline. 60 Eur J Pharm Biopharm. 373 (2005)); pH adjustment, e.g., pH titration and/or exposure to an electric field (see, e.g., U.S. Patent App. No. US2011/0171239); heat treatment; shear stress (see, e.g., International App. No.: WO 2011/005381), ultrasound, e.g., sonication (see, e.g., U.S. Patent Application Publication No. U.S. 2010/0178304 and International App. No. WO2008/150861); and any combinations thereof. Content of all of the references listed above is incorporated herein by reference in their entirety.

In some embodiments, the conformation of the silk fibroin can be altered by water annealing. Without wishing to be bound by a theory, it is believed that physical temperature-controlled water vapor annealing (TCWVA) provides a simple and effective method to obtain refined control of the molecular structure of silk biomaterials. The silk materials can be prepared with control of crystallinity, from a low content using conditions at 4° C. (αhelix dominated silk I structure), to highest content of ~60% crystallinity at 100° C. (β-sheet dominated silk II structure). This physical approach covers the range of structures previously reported to govern crystallization during the fabrication of silk materials, yet offers a simpler, green chemistry, approach with tight control of reproducibility. Temperature controlled water vapor annealing is described, for example, in Hu et al., Regulation of Silk Material Strcuture By Temperature Controlled Water Vapor Annealing, Biomacromolecules, 2011, 12(5): 1686-1696, content of which is incorporated herein by reference in its entirety.

In some embodiments, alteration in the conformation of the silk fibroin can be induced by immersing in alcohol, e.g., methanol, ethanol, etc. The alcohol concentration can be at least 10%, at least 20%, at least 30%, at least 40%, at least 50%, at least 60%, at least 70%, at least 80%, at least 90% or 100%. In some embodiment, alcohol concentration is 100%. If the alteration in the conformation is by immersing in a solvent, the silk composition can be washed, e.g., with solvent/water gradient to remove any of the residual solvent that is used for the immersion. The washing can be repeated one, e.g., one, two, three, four, five, or more times.

Alternatively, the alteration in the conformation of the silk fibroin can be induced with sheer stress. The sheer stress can be applied, for example, by passing the silk composition through a needle. Other methods of inducing conformational changes include applying an electric field, applying pressure, or changing the salt concentration.

The treatment time for inducing the conformational change can be any period of time to provide a desired silk II (beta-sheet crystallinity) content. In some embodiments, the treatment time can range from about 1 hour to about 12 hours, from about 1 hour to about 6 hours, from about 1 hour to about 5 hours, from about 1 hour to about 4 hours, or from about 1 hour to about 3 hours. In some embodiments, the sintering time can range from about 2 hours to about 4 hours or from 2.5 hours to about 3.5 hours.

When inducing the conformational change is by solvent immersion, treatment time can range from minutes to hours. For example, immersion in the solvent can be for a period of at least about 15 minutes, at least about 30 minutes, at least about 1 hour, at least about 2 hours, at least 3 hours, at least about 6 hours, at least about 18 hours, at least about 12 hours, at least about 1 day, at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 13 days, or at least about 14 days. In some embodiments, immersion in the solvent can be for a period of about 12 hours to about seven days, about 1 day to about 6 days, about 2 to about 5 days, or about 3 to about 4 days.

After the treatment to induce the conformational change, silk fibroin can comprise a silk II beta-sheet crystallinity content of at least about 5%, at least about 10%, at least about 20%, at least about 30%, at least about 40%, at least about 50%, at least about 60%, at least about 70%, at least about 80%, at least about 90%, or at least about 95% but not 100% (i.e., all the silk is present in a silk II beta-sheet conformation). In some embodiments, silk is present completely in a silk II beta-sheet conformation, i.e., 100% silk II beta-sheet crystallinity.

In some embodiments, the silk composition for compaction can comprise one or more (e.g., one, two, three, four, five or more) additives. Without wishing to be bound by a theory additive can provide one or more desirable properties to an article of manufacture, e.g., strength, flexibility, ease of processing and handling, biocompatibility, bioresorability, lack of air bubbles, surface morphology, and the like, prepared from the compacted composition. The additive can be covalently or non-covalently linked with silk and can be integrated homogenously or heterogeneously within the silk composition.

An additive can be selected from small organic or inorganic molecules; saccharines; oligosaccharides; polysaccharides; biological macromolecules, e.g., peptides, proteins, and peptide analogs and derivatives; peptidomimetics; antibodies and antigen binding fragments thereof; nucleic acids; nucleic acid analogs and derivatives; glycogens or other sugars; immunogens; antigens; an extract made from biological materials such as bacteria, plants, fungi, or animal cells; animal tissues; naturally occurring or synthetic compositions; and any combinations thereof. Furthermore, the additive can be in any physical form. For example, the additive can be in the form of a particle, a fiber, a film, a gel, a mesh, a mat, a non-woven mat, a powder, a liquid, or any combinations thereof. In some embodiments, the additive is a particle.

Total amount of additives in the composition can be from about 0.1 wt % to about 99 wt %, from about 0.1 wt % to about 70 wt %, from about 5 wt % to about 60 wt %, from about 10 wt % to about 50 wt %, from about 15 wt % to about 45 wt %, or from about 20 wt % to about 40 wt %, of the total silk composition. In some embodiments, ratio of silk to additive in the composition can range from about 50:1 (w/w) to about 1:50 (w/w), from about 25:1 (w/w) to about 1:25 (w/w), from about 20:1 (w/w) to about 1:20 (w/w), from about 10:1 (w/w) to about 1:10 (w/w), or from about 5:1 (w/w) to about 1:5 (w/w).

In some embodiments, the additive is a calcium phosphate material (CaP). As used herein, the term "calcium phosphate material" refers to any material composed of calcium and phosphate ions. The term "calcium phosphate material" is intended to include naturally occurring and synthetic materials composed of calcium and phosphate ions. The ratio of calcium to phosphate ions in the calcium phosphate materials is preferably selected such that the resulting material is able to perform its intended function. For convenience, the calcium to phosphate ion ratio is abbreviated as the "Ca/P ratio." In some embodiments, the Ca/P ratio can range from about 1:1 to about 1.67 to 1. In some embodiments, the calcium phosphate material can be calcium deficient. By "calcium deficient" is meant a calcium phosphate material with a calcium to phosphate ratio of less than about 1.6 as compared to the ideal stoichiometric value of approximately 1.67 for hydroxyapatite The calcium phosphate material can be in the form of particles. Without limitations, the calcium phosphate material particles can be of any desired size. In some embodiments, the calcium phosphate material particles can have a size ranging from about 0.01 µm to about 1000 µm, about 0.05 µm to about 500 µm, about 0.1 µm to about 250 µm, about 0.25 µm to about 200 µm, or about 0.5 µm to about 100 µm. Further, the calcium phosphate material particle can be of any shape or form, e.g., spherical, rod, elliptical, cylindrical, capsule, or disc.

In some embodiments, the calcium phosphate material particle is a microparticle or a nanoparticle. In some embodiments, the calcium phosphate material particle has a particle size of about 0.01 µm to about 1000 µm, about 0.05 µm to about 750 µm, about 0.1 µm to about 500 µm, about 0.25 µm to about 250 µm, or about 0.5 µm to about 100 µm. In some embodiments, the silk particle has a particle size of about 0.1 nm to about 1000 nm, about 0.5 nm to about 500 nm, about 1 nm to about 250 nm, about 10 nm to about 150 nm, or about 15 nm to about 100 nm.

The calcium phosphate material can be selected, for example, from one or more of brushite, octacalcium phosphate, tricalcium phosphate (also referred to as tricalcic phosphate and calcium orthophosphate), calcium hydrogen phosphate, calcium dihydrogen phosphate, apatite, and/or hydroxyapatite. Further, tricalcium phosphate (TCP) can be in the alpha or the beta crystal form. In some embodiments, the calcium phosphate material is beta-tricalcium phosphate or apatite, e.g., hydroxyapatite (HA).

The amount of the calcium phosphate material in the silk composition can range from about 1% to about 99% (w/w or w/v). In some embodiments, the amount of the calcium phosphate material in the silk composition can be from about 5% to about 95% (w/w or w/v), from about 10% to about 90% (w/w or w/v), from about 15% to about 80% (w/w or w/v), from about 20% to about 75% (w/w or w/v), from about 25% to about 60% (w/w or w/v), or from about 30% to about 50% (w/w or w/v). In some embodiments, the amount of the calcium phosphate material in the silk composition can be less than 20%.

Generally, the silk composition can comprise any ratio of silk to calcium phosphate material. For example, the ratio of silk to calcium phosphate material in the composition can range from about 1000:1 to about 1:1000. The ratio can be based on weight or moles. In some embodiments, the ratio of silk to calcium phosphate material in the solution can range from about 500:1 to about 1:500 (w/w), from about 250:1 to about 1:250 (w/w), from about 50:1 to about 1:200 (w/w), from about 10:1 to about 1:150 (w/w) or from about 5:1 to about 1:100 (w/w).

In some embodiments, the additive can be a silk-based material. The silk-based material can be selected from the group consisting of silk fibers, micro-sized silk fibers, unprocessed silk fibers, silk particles, and any combinations thereof.

In some embodiments, the additive is a silk fiber. While the use of silk fibers is described in for example, US patent application publication no. US20110046686, the previously described materials do not provide machinable silk materials as disclosed in the present disclosure.

In some embodiments, the silk fibers are microfibers or nanofibers. In some embodiments, the additive is micron-sized silk fiber (10-600 µm). Micron-sized silk fibers can be obtained by hydrolyzing the degummed silk fibroin or by increasing the boing time of the degumming process. Alkali hydrolysis of silk fibroin to obtain micron-sized silk fibers is described for example in Mandal et al., PNAS, 2012, doi: 10.1073/pnas.1119474109; U.S. Provisional Application No. 61/621,209, filed Apr. 6, 2012; and PCT application no. PCT/US13/35389, filed Apr. 5, 2013, content of all of which is incorporated herein by reference. Because regenerated silk fibers made from HFIP silk solutions are mechanically strong, the regenerated silk fibers can also be used as additive.

In some embodiments, the silk fiber is an unprocessed silk fiber, e.g., raw silk or raw silk fiber. The term "raw silk" or "raw silk fiber" refers to silk fiber that has not been treated to remove sericin, and thus encompasses, for example, silk fibers taken directly from a cocoon Thus, by unprocessed silk fiber is meant silk fibroin, obtained directly from the silk gland. When silk fibroin, obtained directly from the silk gland, is allowed to dry, the structure is referred to as silk I in the solid state. Thus, an unprocessed silk fiber comprises silk fibroin mostly in the silk I conformation. A regenerated or processed silk fiber on the other hand comprises silk fibroin having a substantial silk II or beta-sheet crystallinity.

Because implantation and post-surgical imaging of current resorbable fixation devices is a problem, the article of manufacture, e.g., medical devices such as orthopedic screws or other fasteners can be enhanced with iron particles. Accordingly, in some embodiments, the additive is an iron particle. Without wishing to be bound by a theory, it is believed that the iron particles can help the surgeon during implantation due to a magnetic screw that can be attracted to a screw driver head. Further, once the surgery is complete, the surgeon could quickly check that all components are properly placed and have not migrated or failed with a simple magnetic sensor. This would allow for a first pass check of surgical errors and allow the surgeon to reopen the wound and fix the problem before the patient leaves the operating room. This would save on time, money, and recovery time.

In some embodiments, the additive is a biocompatible polymer. Exemplary biocompatible polymers include, but are not limited to, a poly-lactic acid (PLA), poly-glycolic acid (PGA), poly-lactide-co-glycolide (PLGA), polyesters, poly(ortho ester), poly(phosphazine), poly(phosphate ester), polycaprolactone, gelatin, collagen, fibronectin, keratin, polyaspartic acid, alginate, chitosan, chitin, hyaluronic acid, pectin, polyhydroxyalkanoates, dextrans, and polyanhydrides, polyethylene oxide (PEO), poly(ethylene glycol) (PEG), triblock copolymers, polylysine, alginate, polyaspartic acid, any derivatives thereof and any combinations thereof. Other exemplary biocompatible polymers amenable to use according to the present disclosure include those described for example in U.S. Pat. Nos. 6,302,848; 6,395,734; 6,127,143; 5,263,992; 6,379,690; 5,015,476; 4,806,355; 6,372,244; 6,310,188; 5,093,489; 387,413; 6,325,810; 6,337,198; 6,267,776; 5,576,881; 6,245,537; 5,902,800; and 5,270,419, content of all of which is incorporated herein by reference.

In some embodiments, the biocompatible polymer is PEG or PEO. As used herein, the term "polyethylene glycol" or "PEG" means an ethylene glycol polymer that contains about 20 to about 2000000 linked monomers, typically about 50-1000 linked monomers, usually about 100-300. PEG is also known as polyethylene oxide (PEO) or polyoxyethylene (POE), depending on its molecular weight. Generally PEG, PEO, and POE are chemically synonymous, but historically PEG has tended to refer to oligomers and polymers with a molecular mass below 20,000 g/mol, PEO to polymers with a molecular mass above 20,000 g/mol, and POE to a polymer of any molecular mass. PEG and PEO are liquids or low-melting solids, depending on their molecular weights. PEGs are prepared by polymerization of ethylene oxide and are commercially available over a wide range of molecular weights from 300 g/mol to 10,000,000 g/mol. While PEG and PEO with different molecular weights find use in different applications, and have different physical properties (e.g. viscosity) due to chain length effects, their chemical properties are nearly identical. Different forms of PEG are also available, depending on the initiator used for the polymerization process—the most common initiator is a monofunctional methyl ether PEG, or methoxypoly(ethylene glycol), abbreviated mPEG. Lower-molecular-weight PEGs are also available as purer oligomers, referred to as monodisperse, uniform, or discrete PEGs are also available with different geometries.

As used herein, the term PEG is intended to be inclusive and not exclusive. The term PEG includes poly(ethylene glycol) in any of its forms, including alkoxy PEG, difunctional PEG, multiarmed PEG, forked PEG, branched PEG, pendent PEG (i.e., PEG or related polymers having one or more functional groups pendent to the polymer backbone), or PEG With degradable linkages therein. Further, the PEG backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, pentaerythritol and sorbitol. The central branch moiety can also be derived from several amino acids, such as lysine. The branched poly(ethylene glycol) can be represented in general form as R(-PEG-OH)m in which R represents the core moiety, such as glycerol or pentaerythritol, and m represents the number of arms. Multiarmed PEG molecules, such as those described in U.S. Pat. No. 5,932,462, which is incorporated by reference herein in its entirety, can also be used as biocompatible polymers.

Some exemplary PEGs include, but are not limited to, PEG20, PEG30, PEG40, PEG60, PEG80, PEG100, PEG115, PEG200, PEG 300, PEG400, PEG500, PEG600, PEG1000, PEG1500, PEG2000, PEG3350, PEG4000, PEG4600, PEG5000, PEG6000, PEG8000, PEG11000, PEG12000, PEG15000, PEG 20000, PEG250000, PEG500000, PEG100000, PEG2000000 and the like. In some embodiments, PEG is of MW 10,000 Dalton. In some embodiments, PEG is of MW 100,000, i.e. PEO of MW 100,000.

In some embodiments, the additive is an enzyme that hydrolyzes silk fibroin. Without wishing to be bound by a theory, such enzymes can be used to control the degradation of the article of manufacture.

Article of Manufacture

Silk-based materials can be used to produce tissue scaffolds for tissue engineering applications. While these tissue scaffolds take advantage of the biocompatibility, tunable degradation, and other properties of silk, in some embodiments, they typically cannot withstand the loading conditions experienced by structural tissue (e.g., bone) in the body. Accordingly, mechanically robust silk materials are developed, and such material formats can range from monolithic to composite structures (silk-silk composites: silk reinforcing phase bound by a second silk material phase).

One application area for robust monolithic and composite silk material is in creating tissue engineering scaffolds for human tissue repair/replacement in areas where in vivo physiological loading conditions may be significant. For example, such material can be used to replace the traditional metal plate and screw components used in a reconstructive orthopedic surgery. Other biomedical applications include usage as an internal fracture stabilizer (smart splint used as an in vivo brace) or void filling where bone defects or disease have compromised mechanical stability.

Hard, strong, lightweight, and biodegradable monolithic and composite silk materials are not limited to biomedical applications. Machine components, such as nuts, bolts, and gears could potentially be constructed of silk. Everyday consumer items, such as biodegradable dishware, plastic ware, or food containers could be silk-based. Given the ability to mold the silk materials described, fairly complex shapes can be created, along with the ability to emboss and imprint images, numbers, and codes. The properties of the silk material can be enhanced and specifically tailored through the addition of other material phases. For example, short or continuous silk bave fiber can be incorporated in a composite construct to enhance material toughness. Optically clear fiber (including silk-based material) can be embedded to provide sensing and information transmission capability. By combining multiple silk material formats, entirely unique products can be fabricated, e.g., construction of a 100% silk apparel and/or accessories. In one embodiment, a 100% silk shoe can be fabricated by combining multiple silk material formats: for example, the hard monolithic and composite silk materials can be combined with silk foams, films, and fibers to make the desired shoe form.

Accordingly, the disclosure also provides an article of manufacture prepared by the method described herein. The article of manufacture prepared according the method described herein is biocompatible and/or at least partially bioresorbable. As used herein, the term "biocompatible" refers to a material that does not elicit a substantial immune response in the host.

By "bioresorbable" is meant the ability of a material to be resorbed or remodeled in vivo. The resorption process involves degradation and elimination of the original implant material through the action of body fluids, enzymes or cells. The resorbed materials can be used by the host in the formation of new tissue, or it can be otherwise re-utilized by the host, or it can be excreted. The article of manufacture described herein can have a resorption half-life of approximately 6 months to approximately 12 months. In some embodiments, the article of manufacture has a resorption half-life of approximately 9 months. The article of manufacture can be completely resorbed in approximately 12 months to approximately 24 months. In some embodiments the material is completely resorbed in approximately 12 months.

In some embodiments, the article of manufacture described herein has compressive strength, compressive toughness and compressive elastic modulus values approximate to those of healthy human bone and enables immediate load-bearing. Without wishing to be bound by a theory, load-bearing properties can also prevent unwanted resorption of adjacent bone resulting from high local stress concentration or stress-shielding.

Compressive toughness is the capacity of a material to resist fracture when subjected to axially directed pushing forces. By definition, the compressive toughness of a material is the ability to absorb mechanical (or kinetic) energy up to the point of failure. Toughness is measured in units of joules per cubic meter ($Jm^{-3}$) and can be measured as the area under a stress-strain curve. In some embodiments, the article of manufacture described herein has a compressive toughness of about 1 kJ m$^{-3}$ to about 20 kJm$^{-3}$ or about 1 kJm$^{-3}$ to approximately 5 kJm$^{-3}$ at 6% strain as measured by the J-integral method. In one embodiment, article of manufacture has a compressive toughness of about 1.3 kJm$^{-3}$, which is the approximate compressive toughness of healthy bone.

Compressive strength is the capacity of a material to withstand axially directed pushing forces. By definition, the compressive strength of a material is that value of uniaxial compressive stress reached when the material fails completely. A stress-strain curve is a graphical representation of the relationship between stress derived from measuring the load applied on the sample (measured in MPa) and strain derived from measuring the displacement as a result of compression of the sample. The ultimate compressive strength of the material can depend upon the target site of implantation. For example, if the material is for placement next to osteoporotic cancellous bone, to avoid high stress accumulation and stress shielding, the material can comprise a compressive strength (stress to yield point) of approximately 0.1 MPa to approximately 2 MPa. If the material is intended for placement next to healthy cancellous bone, the material can comprise an ultimate compressive strength (stress to yield point) of approximately 5 MPa. Alternatively, if the material is intended for placement next to cortical bone, the material can comprise an ultimate compressive strength (stress to yield point) of at least 40 MPa.

Generally, the article of manufacture described herein comprises an ultimate compressive strength (stress to yield point) of at least 5 MPa, at least 10 MPa, at least 15 MPa, at least 20 MPa, at least 25 MPa, at least 30 MPa, at least 35 MPa, at least 40 MPa, at least 45 MPa, at least 50 MPa, at least 55 MPa, at least 60 MPa, at least 65 MPa, at least 70 MPa, at least 75 MPa, at least 80 MPa, at least 85 MPa, at least 90 MPa, at least 95 MPa, at least 100 MPa, at least 105 MPa, at least 110 MPa, at least 115 MPa, at least 120 MPa, at least 125 MPa, at least 130 MPa, at least 135 MPa, at least 140 MPa, at least 145 MPa, at least 150 MPa, or at least 155 MPa.

For example, the article of manufacture described herein comprises an ultimate compressive strength of about 5 MPa to about 140 MPa, about 20 MPa to about 130 MPa, from about 60 MPa to about 125 MPa, or from about 90 to about 120 MPa. In some embodiments, the article of manufacture described herein comprises an ultimate compressive strength (stress to yield point) of at least 100 MPa. In one embodiment, the article of manufacture described herein comprises an ultimate compressive strength (stress to yield point) of approximately 104 MPa. In some embodiments, the article of manufacture described herein has a compressive strength of from about 20 MPa to about 130 MPa at 5% strain.

Compressive elastic modulus is the mathematical description of the tendency of a material to be deformed elastically (i.e. non-permanently) when a force is applied to it. The Young's modulus (E) describes tensile elasticity, or the tendency of a material to deform along an axis when opposing forces are applied along that axis; it is defined as the ratio of tensile stress to tensile strain (measured in MPa) and is otherwise known as a measure of stiffness of the material. The elastic modulus of an object is defined as the slope of the stress-strain curve in the elastic deformation region. The article of manufacture described herein can comprise a compressive elastic modulus of between approximately 100 MPa and approximately 5,000 MPa GPa at 5% strain. In some embodiments, the article of manufacture described herein comprises a compressive elastic modulus of between approximately 200 MPa and 750 MPa, between approximately 250 MPa and 700 MPa, between approximately 300 MPa and 650 MPa, between approximately 400 MPa and 600 MPa, or between approximately 450 MPa and 550 MPa at 5% strain.

In some embodiments, article of manufacture described herein has a mean compressive elastic modulus of about 525 MPa. In some embodiments, the article of manufacture described herein can comprise a compressive elastic modulus of at least 100 MPa, at least 150 MPa, at least 200 MPa, at least 250 MPa, at least 300 MPa, at least 350 MPa, at least 400 MPa, at least 450 MPa, at least 500 MPa, or at least 525 MPa.

Density of the article of manufacture can range from about 1 $g/cm^3$ to about 10 $g/cm^3$. For example, the density can be between about 1.05 $g/cm^3$ to about 5 $g/cm^3$, between about 1.1 $g/cm^3$ to about 2.5 $g/cm^3$, between about 1.2 $g/cm^3$ to about 2.0 $g/cm^3$, between about 1.25 $g/cm^3$ to about 1.5 $g/cm^3$. In some embodiments, density of the article of manufacture is about 1.32 $g/cm^3$.

The article of manufacture can be used for medical applications, e.g. medical devices, or the article can be for non-medical applications.

As used herein, the term medical device is intended to encompass all types of medical devices, including those used in connection with either external or internal treatment of a mammal. Medical devices used in the external treatment of a mammal include, but are not limited to, wound dressings, burn dressings or other skin coverings, and surgical thread. Medical devices used in the internal treatment of a mammal include, but are not limited to, vascular grafts, stents, catheters, valves, artificial joints, artificial organs, surgical thread, and the like.

Exemplary medical devices include, but are not limited to, an orthopedic implant, a facial implant, a nasal implant (e.g., for nasal reconstruction), a suture anchor, a dental implant, a Swanson prosthetic, and any combinations thereof. In some embodiments, the article of manufacture is a continuous, one-phase suture anchor.

As used herein, the term "orthopedic implant" includes within its scope any device intended to be implanted into the body of a vertebrate animal, in particular a mammal such as a human, for preservation and restoration of the function of the musculoskeletal system, particularly joints and bones, including the alleviation of pain in these structures. Exemplary orthopedic implants include, but are not limited to, orthopedic screws, orthopedic plates, orthopedic rods, orthopedic tulips, or any combinations thereof.

In one embodiments, the article of manufacture is a tapping screw, e.g., self-tapping screw.

In some embodiments, the article of manufacture is a suture anchor. Suture anchors are composed of an anchor, eyelet, and suture. The anchor is inserted to the bone which can be a screw mechanism or interference fit and the eyelet is the hole or loop in the anchor through which the suture passes.

As used herein, the term "dental implant" includes within its scope any device intended to be implanted into the oral cavity of a vertebrate animal, in particular a mammal such as a human, in tooth restoration procedures. Dental implants can also be denoted as dental prosthetic devices. Generally, a dental implant is composed of one or several implant parts. For instance, a dental implant usually comprises a dental fixture coupled to secondary implant parts, such as an abutment and/or a dental restoration such as a crown, bridge or denture. However, any device, such as a dental fixture, intended for implantation can alone be referred to as an implant even if other parts are to be connected thereto. Dental implants are presently preferred embodiments.

Bone screws consist of a thread portion and head used for insertion and stabilization of associated equipment such as bone plates.

The Swanson Finger Joint Implant is a flexible intramedullary-stemmed one-piece implant that helps restore function to hands and wrists disabled by rheumatoid, degenerative or traumatic arthritis. It is composed of a silicone elastomer and its primary function is to help maintain proper joint space and alignment with good lateral stability and minimal flexion-extensional restriction. These implants bear minimal load as the majority of the compressive loads are distributed to the bones.

A nasal reconstruction is performed in order to create an aesthetically inconspicuous nose while maintaining function. Structural grafts are often required to provide rigidity to the sidewall and resist lateral collapse and establish nasal contour and projection. Current materials include alloplasts such as silicone and porous high density polyethylene as well has homografts such as alloderm or rib cartilage.

Otoplasty is the process of reconstructing partial or total ear defects typically resulting from congenital hypoplasia, trauma, cancer ablation, and prominent ears. The ears can be reconstructed by using cartilage from the rib cage or an artificial ear can be created. The rib cartilage is carved and wired together using fine stainless steel wire to create a very detailed framework.

In addition to the above-discussed specific medical devices and implants, the method disclosed herein can be used for facial implants (dermal fillers, cheek implants, eye socket), occuloplasty, lip enhancement, reproductive organ plastic surgeries (penile implant, vaginaplasty, sex conversion), buttock augmentation, and other "plastys."

Non-medical applications include manufacturing of dice, thumbtacks, bullets, children's toys (e.g., building blocks, Legos, Checkers, etc. . . . ), and biodegradable plastic alternatives.

In some embodiments, the article of manufacture described herein is osteoconductive. Osteoconductivity is generally defined as the ability of a material to facilitate the migration of osteogenic cells to the surfaces of a scaffold through the fibrin clot established immediately after implantation the material. The porosity of a material affects the osteoconductivity of that material.

In some embodiments, the article of manufacture described herein is osteoinductive. Osteoinductivity is generally defined as the ability to induce non-differentiated stem cells or osteoprogenitor cells (osteoblasts), which is a component of osseous (bone) tissue, to differentiate into osteoblasts. The simplest test of osteoinductivity is the ability to induce the formation of bone in tissue locations such as muscle, which do not normally form bone (ectopic bone growth). It is generally understood that article of manufacture described herein can be made osteoinductive by adding growth factors such as rhBMP-2 (recombinant human bone morphogenic protein-2) to them. The mineralization and the addition of growth factors can affect the osteoinductivity of a material.

In some embodiments, the article of manufacture described herein is osteogenic and shows new bone formation after implantation in vivo. Osteogenesis is the process of laying down new bone material using osteoblasts. Osteoblasts build bone by producing osteoid to form an osteoid matrix, which is composed mainly of Type I collagen. Osseous tissue comprises the osteoid matrix and minerals (mostly with calcium phosphate) that form the chemical arrangement termed calcium hydroxyapatite. Osteoblasts are typically responsible for mineralization of the osteoid matrix to form osseous tissue. Without wishing to be bound by a theory, the osteoconductivity and osteoinductivity of the material has an impact on osteogenesis. The material can show new bone formation within 6 months of implantation in vivo. In some embodiments, the material shows new bone formation within 8 weeks of implantation in vivo.

In some embodiments, the article of manufacture described herein can comprise one or more supplementary material. The supplementary material is selected based upon its compatibility with one or more components of the silk composition and its ability to impart properties (biological, chemical, physical, or mechanical) to the composite, which are desirable for a particular therapeutic purpose or for post-sterilization stability. For example, the supplementary material can be selected to improve tensile strength and hardness, increase fracture toughness, and provide imaging capability of the paste after implantation, hydration, and hardening. The supplementary materials are desirably biocompatible.

The supplementary material can be present in the silk composition in varying amounts and in a variety of physical forms, dependent upon the anticipated therapeutic use. For example, the supplementary material can be in the form of solid structures, such as sponges, meshes, films, fibers, gels, filaments or particles, including microparticles and nanoparticles. The supplementary material itself can be a composite. The supplementary material can be a particulate or liquid additive or doping agent.

In many instances, it is desirable that the supplementary material be bioresorbable. Bioresorbable material for use as supplementary material include, without limitation, polysaccharides, nucleic acids, carbohydrates, proteins, polypeptides, poly($\alpha$-hydroxy acids), poly(lactones), poly(amino acids), poly(anhydrides), poly(orthoesters), poly(anhydride-co-imides), poly(orthocarbonates), poly($\alpha$-hydroxy alkanoates), poly(dioxanones), and poly(phosphoesters). Preferably, the bioresorbable polymer is a naturally occurring polymer, such as collagen, glycogen, chitin, starch, keratins, silk, demineralized bone matrix, and hyaluronic acid; or a synthetic polymer, such as poly(L-lactide) (PLLA), poly(D, L-lactide) (PDLLA), polyglycolide (PGA), poly(lactide-co-glycolide) (PLGA), poly(L-lactide-co-D, L-lactide), poly(D, L-lactide co-trimethylene carbonate), polyhydroxybutyrate (PHB), poly($\epsilon$-caprolactone), poly($\gamma$-valerolactone), poly($\gamma$-butyrolactone), poly(caprolactone), or copolymers thereof. Such polymers are known to bioerode and are suitable for use in the article of manufacture described herein for bone grafts and the like. In addition, bioresorbable inorganic supplementary materials, such as compositions including $SiO_2$, $Na_2O$, $CaO$, $P_2O_5$, $Al_2O_3$ and/or $CaF_2$, can be used, as well as salts, e.g., NaCl, and sugars, e.g., mannitol, and combinations thereof.

Supplementary materials can also be selected from non-resorbable or poorly resorbable materials. Suitable non-resorbable or poorly resorbable materials include, without limitation, dextrans, cellulose and derivatives thereof (e.g., methylcellulose, carboxy methylcellulose, hydroxypropyl methylcellulose, and hydroxyethyl cellulose), polyethylene, polymethylmethacrylate (PMMA), carbon fibers, poly(ethylene glycol), poly(ethylene oxide), poly(vinyl alcohol), poly(vinylpyrrolidone), poly(ethyloxazoline), poly(ethylene oxide)-co-poly(propylene oxide) block copolymers, poly (ethylene terephthalate)polyamide, and lubricants, such as polymer waxes, lipids and fatty acids.

The article of manufacture described herein is also useful for the preparation of delivery vehicles for biologically active agents. In general, the only requirement is that the substance remain active within material during fabrication or be capable of being subsequently activated or re-activated, or that the biologically active agent be added to the material after at the time of implantation of into a host or following fabricatioin of the vehicle.

Biologically active agents that can be incorporated into the article of manufacture described herein include, without limitation, organic molecules, inorganic materials, proteins, peptides, nucleic acids (e.g., genes, gene fragments, gene regulatory sequences, and antisense molecules), nucleoproteins, polysaccharides, glycoproteins, and lipoproteins. Classes of biologically active compounds that can be incorporated into the article of manufacture described herein include, without limitation, anticancer agents, antibiotics, analgesics, anti-inflammatory agents, immunosuppressants, enzyme inhibitors, antihistamines, anti-convulsants, hormones, muscle relaxants, antispasmodics, ophthalmic agents, prostaglandins, anti-depressants, anti-psychotic substances, trophic factors, osteoinductive proteins, growth factors, and vaccines.

In some cases the article of manufacture, e.g. an orthopedic implant needs to be tuned to degrade in a shorter time frame to allow for dynamic transfer of the load back to the healing bone. This could be accomplished numerous different ways such as autoclaving multiple times to degrade the silk fibroin or incorporating enzymes into the constructs that activate upon hydration [28, 33, 34]. Coating the silk devices with bioactive compounds such as BMP-2 and other pharmaceuticals could provide benefits in bone fixation systems. The article of manufacture can also incorporate bioactive compounds such as BMP-2 or antibiotics to promote bone ingrowth [29-31]. Without wishing to be bound by a theory, it is believed that such factors can be used to modulate healing and promote remodeling of bone.

The combination of the silk with bioactive compounds such as enzymes, bone morphogenetic protein 2 (BMP-2), and pharmaceuticals is believed to provide multifunctional benefits not currently utilized in bone fixation systems.

Generally, any therapeutic agent can be encapsulated in the drug delivery vehicle or composition comprising the article of manufacture described herein. As used herein, the term "therapeutic agent" means a molecule, group of molecules, complex or substance administered to an organism for diagnostic, therapeutic, preventative medical, or veterinary purposes. As used herein, the term "therapeutic agent" includes a "drug" or a "vaccine." This term include externally and internally administered topical, localized and systemic human and animal pharmaceuticals, treatments, remedies, nutraceuticals, cosmeceuticals, biologicals, devices, diagnostics and contraceptives, including preparations useful in clinical and veterinary screening, prevention, prophylaxis, healing, wellness, detection, imaging, diagnosis, therapy, surgery, monitoring, cosmetics, prosthetics, forensics and the like. This term can also be used in reference to agriceutical, workplace, military, industrial and environmental therapeutics or remedies comprising selected molecules or selected nucleic acid sequences capable of recognizing cellular receptors, membrane receptors, hormone receptors, therapeutic receptors, microbes, viruses or selected targets comprising or capable of contacting plants, animals and/or humans. This term can also specifically include nucleic acids and compounds comprising nucleic acids that produce a therapeutic effect, for example deoxyribonucleic acid (DNA), ribonucleic acid (RNA), or mixtures or combinations thereof, including, for example, DNA nanoplexes, siRNA, shRNA, aptamers, ribozymes, decoy nucleic acids, antisense nucleic acids, RNA activators, and the like.

The term "therapeutic agent" also includes an agent that is capable of providing a local or systemic biological, physiological, or therapeutic effect in the biological system to which it is applied. For example, the therapeutic agent can act to control infection or inflammation, enhance cell growth and tissue regeneration, control tumor growth, act as an analgesic, promote anti-cell attachment, and enhance bone growth, among other functions. Other suitable therapeutic agents can include anti-viral agents, hormones, antibodies, or therapeutic proteins. Other therapeutic agents include prodrugs, which are agents that are not biologically active when administered but, upon administration to a subject are converted to biologically active agents through metabolism or some other mechanism. Additionally, a silk-based drug delivery composition can contain combinations of two or more therapeutic agents.

A therapeutic agent can include a wide variety of different compounds, including chemical compounds and mixtures of chemical compounds, e.g., small organic or inorganic molecules; saccharines; oligosaccharides; polysaccharides; biological macromolecules, e.g., peptides, proteins, and peptide analogs and derivatives; peptidomimetics; antibodies and antigen binding fragments thereof; nucleic acids; nucleic acid analogs and derivatives; an extract made from biological materials such as bacteria, plants, fungi, or animal cells; animal tissues; naturally occurring or synthetic compositions; and any combinations thereof. In some embodiments, the therapeutic agent is a small molecule.

As used herein, the term "small molecule" can refer to compounds that are "natural product-like," however, the term "small molecule" is not limited to "natural product-like" compounds. Rather, a small molecule is typically characterized in that it contains several carbon-carbon bonds, and has a molecular weight of less than 5000 Daltons (5 kDa), preferably less than 3 kDa, still more preferably less than 2 kDa, and most preferably less than 1 kDa. In some cases it is preferred that a small molecule have a molecular weight equal to or less than 700 Daltons.

Exemplary therapeutic agents include, but are not limited to, those found in *Harrison's Principles of Internal Medicine*, $13^{th}$ Edition, Eds. T. R. Harrison et al. McGraw-Hill N.Y., NY; Physicians' Desk Reference, $50^{th}$ Edition, 1997, Oradell New Jersey, Medical Economics Co.; Pharmacological Basis of Therapeutics, $8^{th}$ Edition, Goodman and Gilman, 1990; United States Pharmacopeia, The National Formulary, USP XII NF XVII, 1990, the complete contents of all of which are incorporated herein by reference.

Therapeutic agents include the herein disclosed categories and specific examples. It is not intended that the category be limited by the specific examples. Those of ordinary skill in the art will recognize also numerous other compounds that fall within the categories and that are useful according to the present disclosure. Examples include a radiosensitizer, a steroid, a xanthine, a beta-2-agonist bronchodilator, an anti-inflammatory agent, an analgesic agent, a calcium antagonist, an angiotensin-converting enzyme inhibitors, a beta-blocker, a centrally active alpha-agonist, an alpha-1-antagonist, an anticholinergic/antispasmodic agent, a vasopressin analogue, an antiarrhythmic agent, an antiparkinsonian agent, an antiangina/antihypertensive agent, an anticoagulant agent, an antiplatelet agent, a sedative, an ansiolytic agent, a peptidic agent, a biopolymeric agent, an antineoplastic agent, a laxative, an antidiarrheal agent, an antimicrobial agent, an antifingal agent, a vaccine, a protein, or a nucleic acid. In a further aspect, the pharmaceutically active agent can be coumarin, albumin, steroids such as betamethasone, dexamethasone, methylprednisolone, prednisolone, prednisone, triamcinolone, budesonide, hydrocortisone, and pharmaceutically acceptable hydrocortisone derivatives; xanthines such as theophylline and doxophylline; beta-2-agonist bronchodilators such as salbutamol, fenterol, clenbuterol, bambuterol, salmeterol, fenoterol; antiinflammatory agents, including antiasthmatic anti-inflammatory agents, antiarthritis antiinflammatory agents, and non-steroidal antiinflammatory agents, examples of which include but are not limited to sulfides, mesalamine, budesonide, salazopyrin, diclofenac, pharmaceutically acceptable diclofenac salts, nimesulide, naproxene, acetaminophen, ibuprofen, ketoprofen and piroxicam; analgesic agents such as salicylates; calcium channel blockers such as nifedipine, amlodipine, and nicardipine; angiotensin-converting enzyme inhibitors such as captopril, benazepril hydrochloride, fosinopril sodium, trandolapril, ramipril, lisinopril, enalapril, quinapril hydrochloride, and moexipril hydrochloride; beta-blockers (i.e., beta adrenergic blocking agents) such as sotalol hydrochloride, timolol maleate, esmolol hydrochloride, carteolol, propanolol hydrochloride, betaxolol hydrochloride, penbutolol sulfate, metoprolol tartrate, metoprolol succinate, acebutolol hydrochloride, atenolol, pindolol, and bisoprolol fumarate; centrally active alpha-2-agonists such as clonidine; alpha-1-antagonists such as doxazosin and prazosin; anticholinergic/antispasmodic agents such as dicyclomine hydrochloride, scopolamine hydrobromide, glycopyrrolate, clidinium bromide, flavoxate, and oxybutynin; vasopressin analogues such as vasopressin and desmopressin; antiarrhythmic agents such as quinidine, lidocaine, tocamide hydrochloride, mexiletine hydrochloride, digoxin, verapamil hydrochloride, propafenone hydrochloride, flecamide acetate, procainamide hydrochloride, moricizine hydrochloride, and disopyramide phosphate; antiparkinsonian agents, such as dopamine, L-Dopa/Carbidopa, selegiline, dihydroergocryptine, pergolide, lisuride, apomorphine, and bromocryptine; antiangina agents and antihypertensive agents such as isosorbide mononitrate, isosorbide dinitrate, propranolol, atenolol and verapamil; anticoagulant and antiplatelet agents such as Coumadin, warfarin, acetylsalicylic acid, and ticlopidine; sedatives such as benzodiazapines and barbiturates; ansiolytic agents such as lorazepam, bromazepam, and diazepam; peptidic and biopolymeric agents such as calcitonin, leuprolide and other LHRH agonists, hirudin, cyclosporin, insulin, somatostatin, protirelin, interferon, desmopressin, somatotropin, thymopentin, pidotimod, erythropoietin, interleukins, melatonin, granulocyte/macrophage-CSF, and heparin; antineoplastic agents such as etoposide, etoposide phosphate, cyclophosphamide, methotrexate, 5-fluorouracil, vincristine, doxorubicin, cisplatin, hydroxyurea, leucovorin calcium, tamoxifen, flutamide, asparaginase, altretamine, mitotane, and procarbazine hydrochloride; laxatives such as senna concentrate, casanthranol, bisacodyl, and sodium picosulphate; antidiarrheal agents such as difenoxine hydrochloride, loperamide hydrochloride, furazolidone, diphenoxylate hdyrochloride, and microorganisms; vaccines such as bacterial and viral vaccines; antimicrobial agents such as penicillins, cephalosporins, and macrolides, antifungal agents such as imidazolic and triazolic derivatives; and nucleic acids such as DNA sequences encoding for biological proteins, and antisense oligonucleotides.

Anti-cancer agents include alkylating agents, platinum agents, antimetabolites, topoisomerase inhibitors, antitumor antibiotics, antimitotic agents, aromatase inhibitors, thymidylate synthase inhibitors, DNA antagonists, farnesyltransferase inhibitors, pump inhibitors, histone acetyltransferase inhibitors, metalloproteinase inhibitors, ribonucleoside reductase inhibitors, TNF alpha agonists/antagonists, endothelinA receptor antagonists, retinoic acid receptor agonists, immuno-modulators, hormonal and anti-hormonal agents, photodynamic agents, and tyrosine kinase inhibitors.

Antibiotics include aminoglycosides (e.g., gentamicin, tobramycin, netilmicin, streptomycin, amikacin, neomycin), bacitracin, corbapenems (e.g., imipenem/cislastatin), cephalosporins, colistin, methenamine, monobactams (e.g., aztreonam), penicillins (e.g., penicillin G, penicillinV, methicillin, natcillin, oxacillin, cloxacillin, dicloxacillin, ampicillin, amoxicillin, carbenicillin, ticarcillin, piperacillin, mezlocillin, azlocillin), polymyxin B, quinolones, and vancomycin; and bacteriostatic agents such as chloramphenicol, clindanyan, macrolides (e.g., erythromycin, azithromycin, clarithromycin), lincomyan, nitrofurantoin, sulfonamides, tetracyclines (e.g., tetracycline, doxycycline, minocycline, demeclocyline), and trimethoprim. Also included are metronidazole, fluoroquinolones, and ritampin.

Enzyme inhibitors are substances which inhibit an enzymatic reaction. Examples of enzyme inhibitors include edrophonium chloride, N-methylphysostigmine, neostigmine bromide, physostigmine sulfate, tacrine, tacrine, 1-hydroxy maleate, iodotubercidin, p-bromotetramiisole, 10-(alpha-diethylaminopropionyl)-phenothiazine hydrochloride, calmidazolium chloride, hemicholinium-3,3,5-dinitrocatechol, diacylglycerol kinase inhibitor I, diacylglycerol kinase inhibitor II, 3-phenylpropargylamine, N°-monomethyl-Larginine acetate, carbidopa, 3-hydroxybenzylhydrazine, hydralazine, clorgyline, deprenyl, hydroxylamine, iproniazid phosphate, 6-MeO-tetrahydro-9H-pyrido-indole, nialamide, pargyline, quinacrine, semicarbazide, tranylcypromine, N,N-diethylaminoethyl-2,2-diphenylvalerate hydrochloride, 3-isobutyl-1-methylxanthne, papaverine, indomethacind, 2-cyclooctyl-2-hydroxyethylamine hydrochloride, 2,3-dichloro-a-methylbenzylamine (DCMB), 8,9-dichloro-2,3,4,5-tetrahydro-1H-2-benzazepine hydrochloride, p-amino glutethimide, p-aminoglutethimide tartrate, 3-iodotyrosine, alpha-methyltyrosine, acetazolamide, dichlorphenamide, 6-hydroxy-2-benzothiazolesulfonamide, and allopurinol.

Antihistamines include pyrilamine, chlorpheniramine, and tetrahydrazoline, among others.

Anti-inflammatory agents include corticosteroids, non-steroidal anti-inflammatory drugs (e.g., aspirin, phenylbutazone, indomethacin, sulindac, tolmetin, ibuprofen, piroxicam, and fenamates), acetaminophen, phenacetin, gold salts, chloroquine, D-Penicillamine, methotrexate colchicine, allopurinol, probenecid, and sulfinpyrazone.

Muscle relaxants include mephenesin, methocarbomal, cyclobenzaprine hydrochloride, trihexylphenidyl hydrochloride, levodopa/carbidopa, and biperiden.

Anti-spasmodics include atropine, scopolamine, oxyphenonium, and papaverine.

Analgesics include aspirin, phenybutazone, idomethacin, sulindac, tolmetic, ibuprofen, piroxicam, fenamates, acetaminophen, phenacetin, morphine sulfate, codeine sulfate, meperidine, nalorphine, opioids (e.g., codeine sulfate, fentanyl citrate, hydrocodone bitartrate, loperamide, morphine sulfate, noscapine, norcodeine, normorphine, thebaine, norbinaltorphimine, buprenorphine, chlomaltrexamine, funaltrexamione, nalbuphine, nalorphine, naloxone, naloxonazine, naltrexone, and naltrindole), procaine, lidocain, tetracaine and dibucaine.

Ophthalmic agents include sodium fluorescein, rose bengal, methacholine, adrenaline, cocaine, atropine, alpha-chymotrypsin, hyaluronidase, betaxalol, pilocarpine, timolol, timolol salts, and combinations thereof Prostaglandins are art recognized and are a class of naturally occurring chemically related, long-chain hydroxy fatty acids that have a variety of biological effects.

Anti-depressants are substances capable of preventing or relieving depression. Examples of anti-depressants include imipramine, amitriptyline, nortriptyline, protriptyline, desipramine, amoxapine, doxepin, maprotiline, tranylcypromine, phenelzine, and isocarboxazide.

Trophic factors are factors whose continued presence improves the viability or longevity of a cell. Trophic factors include, Without limitation, platelet-derived growth factor (PDGP), neutrophil-activating protein, monocyte chemoattractant protein, macrophage-inflammatory protein, platelet factor, platelet basic protein, and melanoma growth stimulating activity; epidermal growth factor, transforming growth factor (alpha), fibroblast growth factor, platelet-derived endothelial cell growth factor, insulin-like growth factor, glial derived growth neurotrophic factor, ciliary neurotrophic factor, nerve growth factor, bone growth/cartilage-inducing factor (alpha and beta), bone morphogenetic proteins, interleukins (e.g., interleukin inhibitors or interleukin receptors, including interleukin 1 through interleukin 10), interferons (e.g., interferon alpha, beta and gamma), hematopoietic factors, including erythropoietin, granulocyte colony stimulating factor, macrophage colony stimulating factor and granulocyte-macrophage colony stimulating factor; tumor necrosis factors, and transforming growth factors (beta), including beta-1, beta-2, beta-3, inhibin, and activin.

Hormones include estrogens (e.g., estradiol, estrone, estriol, diethylstibestrol, quinestrol, chlorotrianisene, ethinyl estradiol, mestranol), anti-estrogens (e.g., clomiphene, tamoxifen), progestins (e.g., medroxyprogesterone, norethindrone, hydroxyprogesterone, norgestrel), antiprogestin (mifepristone), androgens (e.g, testosterone cypionate, fluoxymesterone, danazol, testolactone), anti-androgens (e.g., cyproterone acetate, flutamide), thyroid hormones (e.g., triiodothyronne, thyroxine, propylthiouracil, methimazole, and iodixode), and pituitary hormones (e.g., corticotropin, sumutotropin, oxytocin, and vasopressin). Hormones are commonly employed in hormone replacement therapy and/or for purposes of birth control. Steroid hormones, such as prednisone, are also used as immunosuppressants and anti-inflammatories.

The biologically active agent can be an osteogenic protein. Accordingly, in some embodiments, the biologically active agent is desirably selected from the family of proteins known as the transforming growth factors beta (TGF-[3) superfamily of proteins, which includes the activins, inhibins and bone morphogenetic proteins (BMPs). Most preferably, the active agent includes at least one protein selected from the subclass of proteins known generally as BMPs, which have been disclosed to have osteogenic activity, and other growth and differentiation type activities. These BMPs include BMP proteins BMP-2, BMP-3, BMP-4, BMP5, BMP-6 and BMP-7, disclosed for instance in U.S. Pat. Nos. 5,108,922; 5,013,649; 5,116,738; 5,106,748; 5,187,076; and 5,141,905; BMP-8, disclosed in PCT publication WO91/18098; and BMP-9, disclosed in PCT publication WO93/00432, BMP-10, disclosed in PCT application WO94/26893; BMP-11, disclosed in PCT application WO94/26892, or BMP-12 or BMP-13, disclosed in PCT application WO 95/16035; BMP-14; BMP-15, disclosed in U.S. Pat. No. 5,635,372; or BMP-16, disclosed in U.S. Pat. No. 5,965,403. Other TGF-β proteins, which can be used include Vgr-2, Jones et al., Mol. Endocrinol. 611961 (1992), and any of the growth and differentiation factors (GDFs), including those described in PCT applications WO94/15965; WO94/15949; WO95/01801; WO95/01802; WO94/21681; WO94/15966; WO95/10539; WO96/01845; WO96/02559 and others. Also useful in the invention can be BIP, disclosed in WO94/01557; HP00269, disclosed in JP Publication number: 7-250688; and BMP-14 (also known as MP52, CDMP1, and GDF5), disclosed in PCT application WO93/16099. The disclosures of all of the above applications are incorporated herein by reference. Subsets of BMPs which can be used include BMP-2, BMP-3, BMP-3b, BMP-4, BMP-5, BMP-6, BMP-7, BMP-8, BMP-9, BMP-10, BMP-11, BMP-12, BMP-13, BMP-14, BMP-15, BMP-16, BMP-17, and BMP18. Other osteogenic agents known in the art can also be used, such as teriparatide (FORTEO™), CHRYSALIN®, prostaglandin E2, or LIM protein, among others.

The biologically active agent can be recombinantly produced, or purified from a protein composition. The active agent, if a TGF-β such as a BMP, or other dimeric protein, can be homodimeric, or can be heterodimeric with other BMPs (e.g., a heterodimer composed of one monomer each of BMP-2 and BMP-6) or With other members of the TGF-β superfamily, such as activins, inhibins and TGF-β1 (e.g., a heterodimer composed of one monomer each of a BMP and a related member of the TGF-β superfamily). Examples of such heterodimeric proteins are described for example in Published PCT Patent Application WO 93/09229, the content of which is incorporated herein by reference.

The active agent can further include additional agents such as the Hedgehog, Frazzled, Chordin, Noggin, Cerberus and Follistatin proteins. These families of proteins are generally described in Sasai et al., Cell 791779-790 (1994) (Chordin); PCT Patent Publication WO94/05800 (Noggin); and Fukui et al., Devel. Biol. 159: 1 31 (1993) (Follistatin). Hedgehog proteins are described in WO96/16668; WO96/17924; and WO95/18856. The Frazzled family of proteins is a recently discovered family of proteins With high homology to the extracellular binding domain of the receptor protein family known as Frizzled. The Frizzled family of genes and proteins is described in Wang et al., 0.1. Biol. Chem. 271:44684476 (1996). The active agent can also include other soluble receptors, such as the truncated soluble receptors disclosed in PCT patent publication WO95/07982. From the teaching of WO95/07982, one skilled in the art will recognize that truncated soluble receptors can be prepared for numerous other receptor proteins. The above publications are hereby incorporated by reference herein.

The amount of osteogenic protein effective to stimulate increased osteogenic activity of present or infiltrating progenitor or other cells will depend upon the size and nature of the defect being treated, as well as the carrier being employed. Generally, the amount of protein to be delivered is in a range of from about 0.1 to about 100 mg; preferably about 1 to about 100 mg; most preferably about 10 to about 80 mg.

Biologically active agents can be introduced into the article of manufacture described herein during or after its formation. Agents can conveniently be mixed into the starting solution prior to fabrication of the article of manufacture described herein. Alternatively, the article of manufacture described herein can be fabricated, shaped into a desired shape, and then exposed to the biologically active agent in solution. This particular approach is particularly well suited for proteins, which are known to have an affinity for apatitic materials. A buffer solution containing the biologically active agent can be employed, instead of water, as the aqueous solution in which the article of manufacture described herein is, for example, irrigated prior to use. Buffers can be used in any pH range, but most often will be used in the range of 5.0 to 8.0 in preferred embodiments the pH will be compatible with prolonged stability and efficacy of the desired biologically active agent and, in most preferred embodiments, will be in the range of 5.5 to 7.4. Suitable buffers include, but are not limited to, carbonates, phosphates (e.g., phosphate buffered saline), and organic buffers such as Tris, HEPES, and MOPS. Most often, the buffer will be selected for its biocompatibility with the host tissues and its compatibility with the biologically active agent. For most applications of nucleic acids, peptides or antibiotics a simple phosphate buffered saline can suffice.

Standard protocols and regimens for delivery of the above listed agents are known in the art. Typically, these protocols are based on oral or intravenous delivery. Biologically active agents are introduced into the vehicle in amounts that allow delivery of an appropriate dosage of the agent to the implant site. In most cases, dosages are determined using guidelines known to practitioners and applicable to the particular agent in question. The exemplary amount of biologically active agent to be included in the article of manufacture described herein is likely to depend on such variables as the type and extent of the condition, the overall health status of the particular patient, the formulation of the active agent, and the bioresorbability of the delivery vehicle used. Standard clinical trials may be used to optimize the dose and dosing frequency for any particular biologically active agent Generally, any amount of the supplementary material, such as a biocompatible polymer, biologically active agent, and therapeutic agent can be loaded into the article of manufacture described herein. For example, from about 0.1 ng to about 1000 mg of the therapeutic agent can be loaded in the article of manufacture described herein. In some embodiment, amount of the supplementary in the silk solution, silk composition or the article of manufacture is selected from the range about from 0.001% (w/w) up to 95% (w/w), preferably, from about 5% (w/w) to about 75% (w/w), and most preferably from about 10% (w/w) to about 60% (w/w) of the total composition. In some embodiments, amount of amount of the supplementary in the article of manufacture described herein is from about 0.01% to about 95% (w/v), from about 0.1% to about 90% (w/w), from about 1% to about 85% (w/w), from about 5% to about 75% (w/w), from about 10% to about 65% (w/w), or from about 10% to about 50% (w/w), of the total composition.

In some embodiments, amount of the supplementary in the article of manufacture described herein is from about 1% to about 99% (w/w), from about 0.05% to about 99% (w/w), from about 0.1% to about 90% (w/w), from about 0.5% to about 85% (w/w), from about 5% to about 80% (w/w), from about 10% to about 60% (w/w) of the total composition. In some embodiments, amount of the supplementary in the silk solution, the silk composition or the article of manufacture is from about 0.1% to about 99% (w/w), from about 1% to about 90% (w/w), from about 2% to about 80% (w/w), from about 5% to about 75% (w/w), from about 5% to about 50% (w/w), from about 0.055% to about 0.1% (w/w) of the total composition.

After preparation, the article of manufacture described herein can be sterilized using conventional sterilization process such as radiation-based sterilization (i.e. gamma-ray), chemical based sterilization (ethylene oxide), autoclaving, or other appropriate procedures. In some embodiments, sterilization process can be with ethylene oxide at a temperature between from about 52° C. to about 55° C. for a time of 8 or less hours. The article of manufacture described herein can also be processed aseptically. Sterile article of manufacture described herein can be packaged in an appropriate sterilize moisture resistant package for shipment.

Without wishing to be bound by a theory, the article of manufacture described herein provides a number of advantages. The material can withstand physiological loading forces; can initiate new bone formation and stimulate healing through direct bone-silk interface; can promote osteogenesis by local delivery of bone morphogenic growth factors; and can achieve complete graft resorption and non-union closure. The methods and articles of manufacture prepared using the same provide a number advantages over the prior art.

Embodiments of the invention can be described by any of the following paragraphs:

1. A method comprising:
    (i) providing a composition comprising silk particles; and
    (ii) compacting the composition by application of pressure into a solid state.
2. The method of paragraph 1, wherein the silk particles are nanoparticles or microparticles.
3. The method of paragraph 1 or 2, wherein the composition comprises silk in an amount of about 25% (w/w) or higher.
4. The method of any of paragraphs 1-3, wherein said pressure is at least 0.05 bar.
5. The method of any of paragraphs 1-4, wherein said compacting is at an elevated temperature.
6. The method of paragraph 5, wherein the elevated temperature is at least 30° C.
7. The method of any of paragraphs 1-6, wherein the composition further comprises a binder.
8. The method of paragraph 7, wherein the binder is a liquid.
9. The method of paragraph 7 or 8, wherein the binder is water.
10. The method of any of paragraphs 7-9, wherein the composition comprises from about 0.1% (w/w) to about 50% (w/w) of the binder.
11. The method of any of paragraphs 1-10, wherein the silk particles comprise degummed silk.
12. The method of any of paragraphs 1-11, wherein the silk particles comprise non-degummed silk.
13. The method of any of paragraphs 1-12, wherein the composition comprises a mixture of silk particles comprising degummed silk and silk particles comprising non-degummed silk.
14. The method of paragraph 13, wherein ratio of degummed silk to non-degummed silk is from about 50:1 to about 1:50 (w/w).
15. The method of paragraph 13 or 14, wherein the ratio of degummed silk to non-degummed silk is from about 1:1 to about 1:20.
16. The method of any of paragraphs 1-15, wherein the composition further comprises an additive.
17. The method of paragraph 16, wherein the additive is selected from the group consisting of small organic or inorganic molecules; saccharines; oligosaccharides; polysaccharides; biological macromolecules, e.g., peptides, proteins, and peptide analogs and derivatives; peptidomimetics; antibodies and antigen binding fragments thereof; nucleic acids; nucleic acid analogs and derivatives; glycogens or other sugars; immunogens; antigens; an extract made from biological materials such as bacteria, plants, fungi, or animal cells; animal tissues; naturally occurring or synthetic compositions; and any combinations thereof.
18. The method of paragraph 16 or 17, wherein the additive is in a form selected from the group consisting of a particle, a fiber, a film, a gel, a hydrogel, a mesh, a mat, a non-woven mat, a powder, a fabric, a scaffold, a tube, a slab or block, a fiber, a foam or a sponge, a needle, a lyophilized article, and any combinations thereof.

19. The method of paragraph 18, wherein the additive particle is a nanoparticle or a microparticle.
20. The method of any of paragraphs 16-19, wherein the additive is a silk-based material.
21. The method of paragraph 20, wherein the silk-based material is selected from the group consisting of silk particles, silk fibers, micro-sized silk fibers, unprocessed silk fibers, and any combinations thereof
22. The method of any of paragraphs 16-21, wherein the composition comprises from about 0.1% to (w/w) to about 99% (w/w) of the additive.
23. The method of any of paragraphs 16-22, wherein ratio of silk to the additive is from about 10:1 to about 1:10 (w/w).
24. The method of any of paragraphs 16-23, wherein the additive is an active agent.
25. The method of paragraph 24, wherein the active agent is a therapeutic agent.
26. The method of any of paragraphs 1-25, wherein the composition is in a mold.
27. The method of any of paragraphs 1-26, further comprising processing the composition to a desired shape after said compacting step.
28. The method paragraph 27, wherein said processing is machining, turning (lathe), rolling, thread rolling, drilling, milling, sanding, punching, die cutting, blanking, broaching, and any combinations thereof.
29. The method of any of paragraphs 1-28, further comprising inducing a conformational change in silk fibroin to a beta-sheet conformation.
30. The method of paragraph 29, wherein said inducing a conformational change comprises solvent immersion, water annealing, water vapor annealing, sonication, pH reduction, exposure to an electric field, controlled slow drying, freeze-drying, compressing, heating, application of shear stress, and any combinations thereof.
31. An article of manufacture comprising silk obtained by the method of any of paragraphs 1-30.
32. The article of manufacture of paragraph 31, wherein the article of manufacture is a medical device.
33. The article of manufacture of paragraph 32, wherein the medical device is selected from the group consisting of an orthopedic implant, a facial implant, a nasal implant, a suture anchor, a dental implant, a Swanson prosthetic, and any combinations thereof.
34. The article of manufacture of paragraph 33, wherein said orthopedic implant is selected from the group consisting of an orthopedic screw, an orthopedic plate, an orthopedic rod, an orthopedic tulip, and any combinations thereof
35. The article of manufacture of any of paragraphs 31-34, wherein the article of manufacture is a tapping screw.
36. The article of manufacture of any of paragraphs 31-35, wherein the article of manufacture is osteoconductive, osteoinductive, osteogenic, or any combinations thereof.
37. The article of manufacture of any of paragraphs 31-36, wherein the article of manufacture is bioresorbable.
38. An article of manufacture comprising silk, wherein the article has a compressive strength of at least 5 MPa; a compressive elastic modulus (Young's modulus) of at least 100 MPa; a shear strength of at least 104 MPa; or a density of at least 1.1 g/cm$^3$.
39. The article of manufacture of paragraph 38, wherein the article of manufacture is obtained by a method of any of paragraphs 1-30.
40. A method for increasing compressive strength, elastic modulus, flexural stiffness, or shear stiffness of a silk-based material, the method comprising:
 (i) providing a composition comprising silk particles; and
 (ii) compacting the composition by application of pressure into a solid state.

Some Selected Definitions

For convenience, certain terms employed herein, in the specification, examples and appended claims are collected herein. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

The term "herein" is meant to include all of the disclosure and is not intended to be limited to a subsection of the disclosure.

As used herein the term "comprising" or "comprises" is used in reference to compositions, methods, and respective component(s) thereof, that are essential to the invention, yet open to the inclusion of unspecified elements, whether essential or not.

The singular terms "a," "an," and "the" include plural referents unless context clearly indicates otherwise. Similarly, the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." The term "about" when used in connection with percentages may mean ±5% of the value being referred to. For example, about 100 means from 95 to 105.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means at least two standard deviation (2SD) away from a reference level. The term refers to statistical evidence that there is a difference. It is defined as the probability of making a decision to reject the null hypothesis when the null hypothesis is actually true.

The term "blank" as used herein means an unfinished part of simple geometry that can later be modified by various machining methods to create the desired shape of the article of manufacture.

The term "drying" means removal of at least a portion of any liquid carrier.

The term "bone repair" refers to any procedure for repairing bone, including those which use a material as a substitute for bone grafts.

The term "bone augmentation" refers to the use of any procedure for adding or building bone.

The term "bone replacement" refers to the use of any procedure for replacing existing bone.

As used herein, the term "microparticle" refers to a particle having a particle size of about 0.01 µm to about 1000 µm.

As used herein, the term "nanoparticle" refers to particle having a particle size of about 0.1 nm to about 1000 nm.

It will be understood by one of ordinary skill in the art that particles usually exhibit a distribution of particle sizes around the indicated "size." Unless otherwise stated, the term "particle size" as used herein refers to the mode of a size distribution of particles, i.e., the value that occurs most frequently in the size distribution. Methods for measuring the particle size are known to a skilled artisan, e.g., by dynamic light scattering (such as photocorrelation spectroscopy, laser diffraction, low-angle laser light scattering (LALLS), and medium-angle laser light scattering (MALLS)), light obscuration methods (such as Coulter analysis method), or other techniques (such as rheology, and light or electron microscopy).

In some embodiments, the particles can be substantially spherical. What is meant by "substantially spherical" is that the ratio of the lengths of the longest to the shortest perpendicular axes of the particle cross section is less than or equal to about 1.5. Substantially spherical does not require a line of symmetry. Further, the particles can have surface texturing, such as lines or indentations or protuberances that are small in scale when compared to the overall size of the particle and still be substantially spherical. In some embodiments, the ratio of lengths between the longest and shortest axes of the particle is less than or equal to about 1.5, less than or equal to about 1.45, less than or equal to about 1.4, less than or equal to about 1.35, less than or equal to about 1.30, less than or equal to about 1.25, less than or equal to about 1.20, less than or equal to about 1.15 less than or equal to about 1.1. Without wishing to be bound by a theory, surface contact is minimized in particles that are substantially spherical, which minimizes the undesirable agglomeration of the particles upon storage. Many crystals or flakes have flat surfaces that can allow large surface contact areas where agglomeration can occur by ionic or non-ionic interactions. A sphere permits contact over a much smaller area.

In some embodiments, the particles have substantially the same particle size. Particles having a broad size distribution where there are both relatively big and small particles allow for the smaller particles to fill in the gaps between the larger particles, thereby creating new contact surfaces. A broad size distribution can result in larger spheres by creating many contact opportunities for binding agglomeration. The particles described herein are within a narrow size distribution, thereby minimizing opportunities for contact agglomeration. What is meant by a "narrow size distribution" is a particle size distribution that has a ratio of the volume diameter of the 90th percentile of the small spherical particles to the volume diameter of the 10th percentile less than or equal to 5. In some embodiments, the volume diameter of the 90th percentile of the small spherical particles to the volume diameter of the 10th percentile is less than or equal to 4.5, less than or equal to 4, less than or equal to 3.5, less than or equal to 3, less than or equal to 2.5, less than or equal to 2, less than or equal to 1.5, less than or equal to 1.45, less than or equal to 1.40, less than or equal to 1.35, less than or equal to 1.3, less than or equal to 1.25, less than or equal to 1.20, less than or equal to 1.15, or less than or equal to 1.1.

Geometric Standard Deviation (GSD) can also be used to indicate the narrow size distribution. GSD calculations involved determining the effective cutoff diameter (ECD) at the cumulative less than percentages of 15.9% and 84.1%. GSD is equal to the square root of the ratio of the ECD less than 84.17% to ECD less than 15.9%. The GSD has a narrow size distribution when GSD<2.5. In some embodiments, GSD is less than 2, less than 1.75, or less than 1.5. In one embodiment, GSD is less than 1.8.

The disclosure is further illustrated by the following examples, which should not be construed as limiting. The examples are illustrative only, and are not intended to limit, in any manner, any of the aspects described herein. The following examples do not in any way limit the invention.

EXAMPLES

Example 1

Exemplary Methods Used for Making Compacted Silk Articles

Fabrication of aluminum powder compaction press and first sample. The compaction press was designed in Solidworks and fabricated from aluminum alloys, except for the piston, which was made from steel. The entire assembly is held together with ¼"-20 screws, which also are used to apply requisite pressure to the piston/sample. The initial sample was made using silk powder that had been pulverized and ball milled. A total of 25% of the powder was generated from degummed silk fibroin, while the remaining 75% was from a non-degumming fibroin source. A total of about 4 grams of powder was mixed with 2 ml of distilled water. The assembled compaction press was stored in an oven for 48 hours at 60° C. The first sample had an excellent disk shape, with smooth surfaces, a dull surface finish, and relatively light coloration. Upon cooling, the sample could not be broken by hand, indicating excellent toughness and strength properties.

Fabrication of an acrylic compaction press. In order to improve the process and make fabrication easier, a new compaction press was designed to be fabricated out of acrylic. In addition, the acrylic material could be cut on a Trotec Speedy 300 laser etcher, allowing for rapid reproduction of future press components. Given the acrylic was not heat resistance, only room temperature testing was appropriate.

Sample fabrication I using acrylic compaction press. A silk powder mixture consisting of 10% degummed fibroin and 90% non-degummed fibroin was utilized. Approximately 5 grams of powder was mixed with 2.5 ml of distilled water and silk solution. The press was then clamped tightly in a vise for 3 days at ambient temperature. When released from the press, the silk construct was not completely dry, and therefore it cracked and flaked. Material that had not flaked away was relatively stiff, but extremely brittle (and easily crumbled under pressure).

Sample fabrication II using acrylic compaction press. A second sample was created using the acrylic press. Instead of ball milled powder, however, commercial pure silk powder was used. This powder was fabricated using hydrolysis, not milling. This powder was very easy to solubilize in distilled water and had a much whiter color than the milled powder. As in the prior experiment, silk powder made of 10% degummed silk fibroin and 90% non-degummed fibroin was utilized. Combining approximately 5 grams of powder with 2.5 ml distilled water, the mixture was clamped in the acrylic press for 4 days. The final silk construct was whiter than the construct fabricated above in Sample fabrication I using acrylic compaction press and the mechanical properties seemed to be worse, with the construct having a chalky feel and the characteristic of crumbling very easily.

Sample at higher temperature using aluminum compaction press. Using the aluminum compaction press, and a powder mixture of 10% degummed silk fibroin/90% non-degummed fibroin, approximately 3 grams of powder were mixed with 2 ml of distilled water. The sample/press was stored in an oven at 120° C. for 48 hours. The resulting sample was darker and appeared to be stiffer and somewhat translucent. The hardness qualitatively seemed higher than with previous samples. The darker color can be attributed to the much higher heat that potentially caused some burning of silk fibroin.

Compaction sample I using water and silk solution. Using the aluminum compaction press and a powder mixture of 25% degummed silk fibroin and 75% non-degummed silk fibroin, approximately 3 grams of powder was mixed with 2.5 ml of distilled water and silk solution. Given the silk solution concentration was approximately 7% w/v, the powder was essentially mixed with a 3.5% w/v silk solution (the distilled water acts to dilute the silk fibroin concentration). The sample and press were stored in an oven at 120° C. for 48 hours. The resulting construct was somewhat burned and cracked. The darker coloration is attributed to the higher temperature (earlier samples using no heating evidenced no color change). Without wishing to be bound by theory, the crack may be developed as a result of the addition of silk solution.

Compaction sample II using water and silk solution. A silk sample was produced using the aluminum compaction press, a powder mixture of 25% degummed silk fibroin and 75% non-degummed silk fibroin, and a dilute silk solution (distilled water added to silk solution). Approximately 3 grams of powder was combined with a total of 2.5 ml dilute silk solution. After storing in an oven at 120° C. oven for 48 hours, the resulting construct was removed. The construct had a glassy surface, was somewhat translucent, and contained many serious cracks. It is likely that the glass-like appearance is due to the temperatures exceeding the material's glass transition temperature. Without wishing to be bound by theory, the cracking can be linked to the addition of silk solution instead of pure water as a binding agent.

New test protocol to develop silk powder compaction. To better understand the effect of various processing parameters on the properties of the resulting silk samples, a test protocol was developed. The two parameters investigated are the specific powder blends of degummed and non-degummed silk fibroin, as well as the amount of distilled water used (no silk solution was to be added in this series of experiments). The first sample created with the test protocol utilized a powder blend of 10% degummed and 90% non-degummed silk fibroin. The powder was mixed with 1 ml of distilled water and the sample/press was stored in an oven at 60° C. oven for 24 hours. One side of the resulting construct was black while slightly translucent and lighter in color on the other. The discoloration was attributed to corrosion that had occurred on the steel piston. The sample was observed to be fairly homogeneous, exhibited high strength and did not contain cracks or flakes.

The second sample created with the test protocol utilized a powder blend of 15% degummed and 85% non-degummed silk fibroin was utilized. Approximately 3 grams of powder was mixed with 2 ml of distilled water and the sample/press was stored in an oven at 90° C. oven for 24 hours. The time in the oven was insufficient to allow the sample to completely dry. It warped and flaked once it started drying outside of the press in ambient conditions. Once dry, the remaining construct exhibited good properties (could not be fractured using hand pressure).

The third sample created with the test protocol utilized a powder blend of 15% degummed and 85% non-degummed silk fibroin was utilized. Approximately 3 grams of powder was mixed with 2 ml of distilled water and the sample/press was stored in an oven at 90° C. oven for 48 hours. The resulting construct was excellent, with smooth surfaces and light color. Due to its excellent geometric stability, stiffness, and toughness, the sample was subjected to machinability tests. A Trotec Speedy 300 Laser Engraver was used to cut some small squares from the sample. Several cutting experiments were run, using varying laser movement speed and power level (the slower the speed and higher the power, the more energy is put into the sample being cut). Although laser cutting could penetrate the construct and provide the desired geometric shape, the cut edges were burned during the process. The silk fibroin also created an unpleasant odor during laser cutting. In a second machining operation, a drill press was used to create small holes through the construct. The drill moved easily through the material, without cracking or chipping the sample. A final machining operation was performed using a DeWalt rotozip tool (handheld milling device). The operation ran smoothly, although the higher rotational speeds of the rotozip tool produced some burning of the machined surfaces.

The fourth sample created with the test protocol utilized a powder blend of 20% degummed and 80% non-degummed silk fibroin. Approximately 3 grams of powder was mixed with 2 ml of distilled water and the sample/press was stored in an oven at 90° C. oven for 48 hours. The resulting construct was excellent, with smooth surfaces and light color. Due to its excellent geometric stability, stiffness, and toughness, this sample was also used to test machinability.

The fifth sample created with the test protocol utilized a powder blend of 25% degummed and 75% non-degummed silk fibroin. Approximately 3 grams of powder was mixed with 2 ml of distilled water and the sample/press was stored in an oven at 90° C. oven for 48 hours. The silk/water mixture had not been evenly distributed in the press, so the resulting construct cracked during the release stage of the process. This is attributed to human error; the sample generally exhibited good mechanical properties otherwise.

New acrylic buffer plate under piston and new sample. To prevent discoloration of samples due to corrosion of the compaction press piston, a thin acrylic disk was laser cut and placed between the piston and sample for subsequent experiments. This design improvement was shown to be effective at preventing further piston corrosion due to exposure to sample moisture and reducing discoloration. A powder blend of 10% degummed and 90% non-degummed silk fibroin was utilized. Approximately 3 grams of powder was mixed with 2 ml of distilled water and the sample/press was stored in an oven at 60° C. oven for 24 hours. For this experiment, an increase in piston pressure was applied (by tightening the hold-down screws described above). Given the rough morphology of the sample, it is assumed that the silk/water combination was poorly mixed. The resulting construct was not homogeneous, although the mechanical performance (stiffness and toughness) appeared to be good.

Fabrication of new aluminum compaction press. In order to fabricate rectangular silk constructs for mechanical testing using powder compaction processing, a new aluminum compaction press was fabricated. The desired geometry was a thin strip with a length-to-width aspect ratio of at least 4. The mechanical testing protocol initially involved 3-point bend testing. In this test, a sample strip is supported underneath by two supports on either end of the sample, while a single upper support in the center places the sample under a bending load. To minimize corrosion issues, the entire press was made from aluminum (no steel parts to generate a brown corrosion product that could discolor the samples). The new press was designed to produce four samples simultaneously, including 4 rectangular wells where the silk powder/binder mixture is placed, "pistons" that transfer pressure from the top plate to the samples and hold-down screws.

Powder compaction with patterned die. The regular geometries described in the prior experiments are useful for a variety of applications. An additional range of applications could be envisioned if embedded features could be created at the surfaces of the silk construct. To explore this potential, a special patterned die insert was created from acrylic (using the single-sample aluminum compaction press). Using an image of an elephant (the Tufts University mascot), the die was created by laser etching on a Trotec Speedy 300 laser engraver. A powder blend of 25% degummed and 75% non-degummed silk fibroin was utilized. Approximately 3 grams of powder was mixed with 2 ml of distilled water which was added to the well, on top of the acrylic die insert. The sample and press were stored in an oven at 90° C. oven for 48 hours. This first patterned die was created with low resolution on the laser engraver, so the silk construct did not contain a clean image of the elephant. It was also determined that the powder was not mixed thoroughly before the addition of water, so material inhomogeneity resulted (making the elephant image difficult to see).

Figure 1B:
Figure 1C:
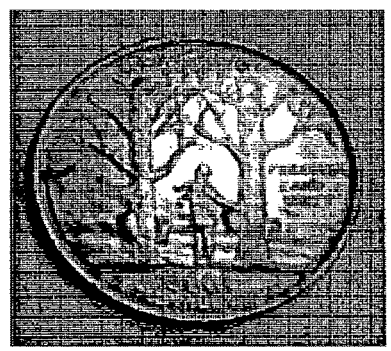
FIGS. 1C and 1D are photographs of silk construct made using a coin as a die insert: the original coin (FIG. 1) and close-up of silk construct exhibiting fine detail (FIG. 1D).
Figure 1D:
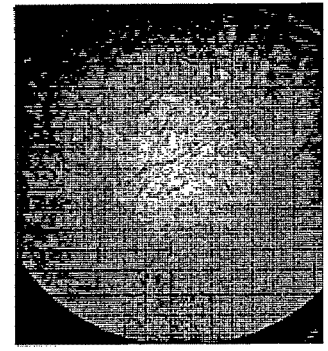

Powder compaction with patterned die II. This experiment utilized the same single-sample aluminum compaction press as described above in Powder compaction with patterned die. However, a higher-resolution image of an elephant was used to create a patterned die. To assist with visibility, a permanent marker was used to color the area surrounding the elephant image on the die. A powder blend of 25% degummed and 75% non-degummed silk fibroin was utilized. Approximately 3 grams of powder was mixed with 2 ml of distilled water which was added to the well, on top of the acrylic die insert. The sample/press was stored in an oven at 90° C. oven for 48 hours. The resulting construct, shown in FIG. 1A (next to the high-resolution acrylic die insert), had excellent geometric stability, with a finely detailed version of the elephant. Using a stereomicroscope (FIG. 1B), the laser etcher's rastering and pulsed response are both visible in the silk construct. FIG. 1D shows another silk construct created using powder compaction and a coin (FIG. 1C) as a die insert. The resulting detail replicated in the silk is excellent.

Samples produced using new multi-sample aluminum compaction press. A series of samples were produced using the newly designed and fabrication multi-sample compaction press. The press has the capability for producing up to 4 strip constructs simultaneously. A powder blend of 25% degummed and 75% non-degummed silk fibroin was utilized for all samples. Approximately 3 grams of powder was mixed with 2 ml of distilled water and the sample/press was stored in an oven at 90° C. oven for 48 hours. Because of insufficient filling of the wells with the powder/water mixture, the first samples were thin and cracked in multiple locations during heating. Doubling the volume of material per compaction well, a second set of 4 samples were produced. While improved, these samples also exhibited cracking during the heating phase of the process. Using the same volume of material, significantly higher pressure was applied in a third round of sample fabrication. These samples were more robust, although some cracking did occur, resulting in fracturing during sample removal from the press.

Example 2

Exemplary Methods Used for Making All-silk Silk Shoes

Figure 2:
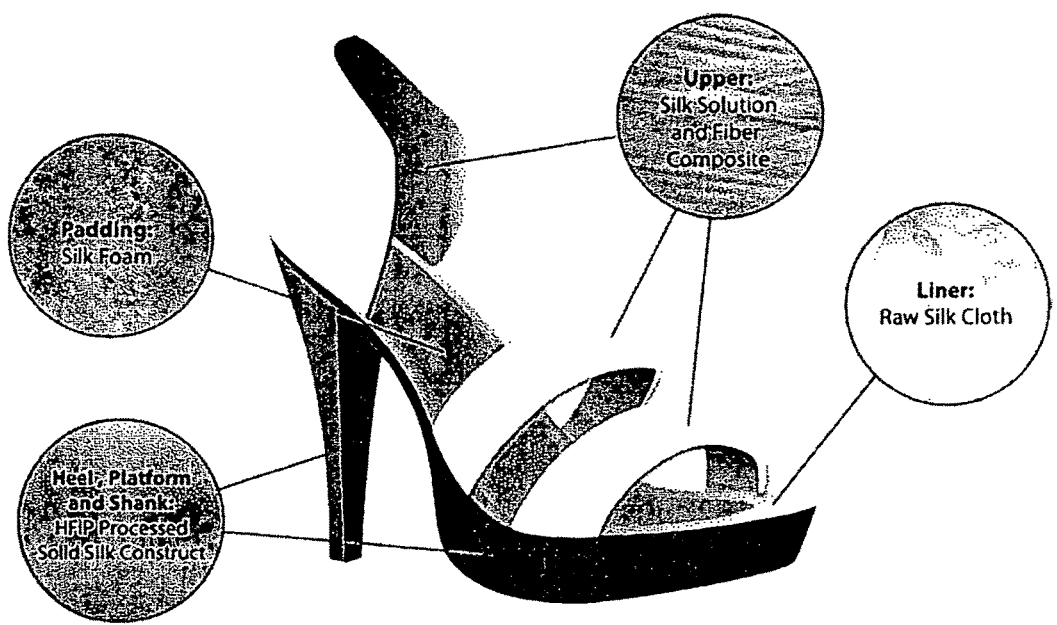
FIG. 2 is a schematic representation of a 100% silk shoe.

The ability to create three-dimensional constructs and/or to perform post-processing operations enables the creation of complex geometries. An exemplary method can relate to the development of an all-silk shoe. This method can form a functional and complete product by bringing many different types of silk-based materials together—foams, fiber/solution composites, the hard constructs described herein, cloth and eletrogelated silk. An exemplary design of the shoe is shown in FIG. 2. In some embodiments, it can support approximately 150 lbs without deforming significantly, and can be a basic high heel design. In other embodiments, the capacity of the shoe can increase to approximately 300 lbs.

Composition of the shoe. The shoe can be composed of several different forms of silk. Each form has a different processing protocol, and each material can be optimized for this specific use. The heel and front platform of the shoe can be made from a solid form of silk processed using HFIP (hexafluoro-2-propanol), as can the bottom portion of the sole. The top portion of the sole can be made from silk foam. This foam can be processed differently to achieve different stiffnesses, and can be used for both the upper part of the sole, and the padding. The upper part of the shoe can be made from a composition of silk fibers and silk solution; combined to form a silk-silk composite with tailored, directional properties.

Figure 3:
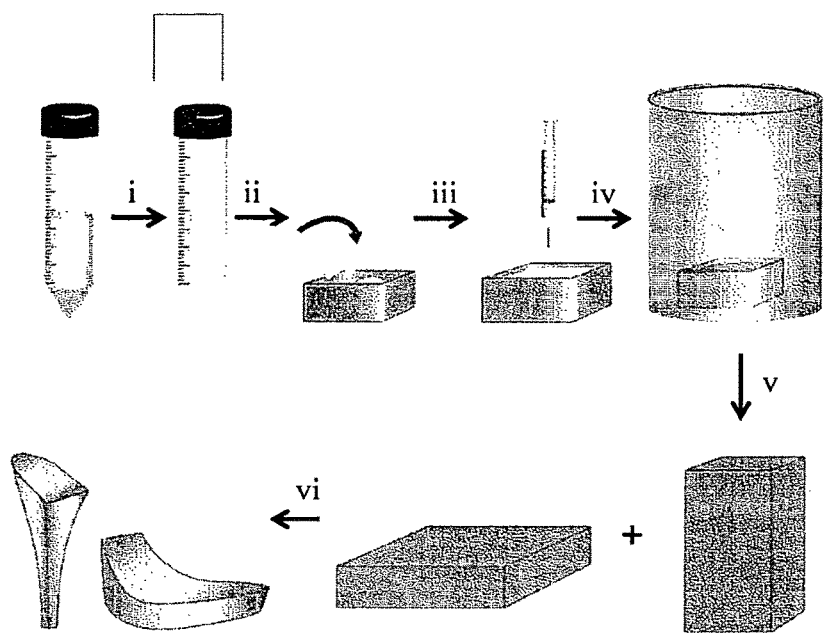

Solid HFIP-processed silk for shoe heels, front platforms and bottoms. FIG. 3 outlines the steps to make shoe heels, front platforms, bottoms or any hard parts of the shoe utilizing HFIP-processed silk. To make this form of silk, there are several steps. First, e.g., silk cocoons are boiled to separate the proteins (degumming). This degummed silk is then dried and dissolved using, e.g., lithium bromide. This dissolved silk can then be dialyzed with water to remove all traces of lithium bromide. At this stage, the silk is referred to as silk solution. The silk solution can then be freeze dried (lyophilized), at which point it becomes silk foam. This foam can then be broken up into small, uniform pieces (pulverized), and packed into a mold of a desired shape. HFIP can be poured on top of the pulverized silk and the mold can be covered. Once this new form of silk is cured, it can be placed in a methanol bath, which washes out the HFIP. The methanol is slowly replaced with water, until all or most methanol has been removed. After this, the piece can be dried. Drying can take any time, as long as several months, depending on the size of the molded piece. As the piece dries, it can shrink.

The HFIP processed silk has been previously used to make small, simple shapes, however it is possible to scale up the production without significant changes in processing. Mold size and shape can be altered to achieve the desired shape, and a new method of drying the piece can be developed to ensure that even drying takes place in all sections, especially in the heel, since the volume to surface area ratio is larger than that of the sole.

For use as the sole and heel of a shoe, this new silk material is preferred to be able to withstand enough force to support a certain amount of weight, as well as the maximum possible impact on the heel due to walking or running. In one embodiment, the shoe can be designed to hold the weight of a 150 lb person. In another embodiment, a maximum weight of 300 lbs can be allowable. In order to show that this material is strong enough, the material properties are characterized. One of the essential properties for this application is the mechanical properties: compressive modulus and bending modulus (stiffness). These values can be found by performing various mechanical tests. A finite element model of the heel can then be made and the required forces simulated to ensure the material will not fail in any way under the maximum load. Chemical testing can also be done in order to ensure the chemicals used during processing are gone from the final product. Other tests can be done on the material in order for the product to be sold commercially. Flammability and burn tests can be performed, as well as tests for solvent resistance. Each of these tests is done on a statistically significant sample size.

When the material is shown to have mechanical properties acceptable for this application, a shoe prototype is constructed. In order to do this, a mold can first be designed and manufactured. The shoe prototype can take significantly longer to cure and dry than the test samples. Once molded, the piece can also be machined, as the shrinkage and warping that occurs during drying can distort the original shape. Any art-recognized methods that can attach the finished pieces made from this material to the rest of the shoe can be used.

Silk foam. The material to be used in the upper part of the sole (the silk foam) can serve as both the support material and the padding in the sole of the shoe. FIG. 4 outlines the steps for this process. Silk foam can be made by preparing silk solution as previously described, then freezing it in a mold and lyophilizing it (freeze drying). Depending on the concentration of the silk solution used, the freezing time, settings of the lyophilizer, and foams of different qualities can be produced. The properties of the formed silk foam can be tuned to match with the padding currently used in shoe manufacture. Compressive modulus, torsional modulus, re-expansion rate after compression, and mode of failure can be taken into account. These properties can then be reproduced in the silk foam by altering variables in the processing. Post processing steps, such as water annealing and methanol treatments, can also be used to tweak certain properties, which affect the crystallinity of the silk. Other qualities to test in this material include the ease of adhesion and sewability of the foam, as well as the mechanical properties in a hydrated environment (due to rain or sweat).

Fiber solution composite. The material to be used as the upper portion of the shoe can be composed of silk fibers woven together and coated in silk solution, as prepared by the protocol explained previously. There are different alterations to this material, including, e.g., the ratio of fiber to solution, the concentration of the solution, and the formation of the woven fiber. Each of these variables can be optimized for the strength and stiffness desired in the final product. FIG. 5 shows the steps for this process.

Attachments and connections. Each of the pieces of the shoe can be produced separately before the assembly of the final product. The heel, upper, platform, padding and lining can be attached to the sole of the shoe. Silk or nonsilk materials can be used to achieve secure attachments. Some of the exemplary attachment methods include, e.g., silk screws made from solid HFIP-processed silk, embedding fibers into foams and solid silk forms, and sewing with silk threads.

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

What is claimed is:

1. A method comprising:
   (i) providing a composition comprising silk particles; and
   (ii) compacting the composition by application of pressure into a solid state;
   wherein the composition comprises a mixture of silk particles comprising degummed silk and silk particles comprising non-degummed silk.

2. The method of claim 1, wherein the silk particles are nanoparticles or microparticles.

3. The method of claim 1, wherein said pressure is at least 0.05 bar.

4. The method of claim 1, wherein said compacting is at an elevated temperature.

5. The method of claim 1, wherein the composition further comprises a binder.

6. The method of claim 5, wherein the composition comprises from about 0.1% (w/w) to about 50% (w/w) of the binder.

7. The method of claim 1, wherein ratio of degummed silk to non-degummed silk is from about 50:1 to about 1:50 (w/w).

8. The method of claim 1, wherein the composition further comprises an additive, wherein the additive is selected from the group consisting of small organic or inorganic molecules; saccharines; oligosaccharides; polysaccharides; biological macromolecules, and derivatives; peptidomimetics; antibodies and antigen binding fragments thereof; nucleic acids; nucleic acid analogs and derivatives; glycogens or other sugars; immunogens; antigens; an extract made from bacteria, plants, fungi, or animal cells; animal tissues; naturally occurring or synthetic compositions; and any combinations thereof.

9. The method of claim 8, wherein the additive is in a form selected from the group consisting of a particle, a fiber, a film, a gel, a hydrogel, a mesh, a mat, a nonwoven mat, a powder, a fabric, a scaffold, a tube, a slab or block, a fiber, a foam or a sponge, a needle, a lyophilized article, and any combinations thereof.

10. The method of claim 8, wherein the additive is a silk-based material.

11. The method of claim 8, wherein the composition comprises from about 0.1% to (w/w) to about 70% (w/w) of the additive.

12. The method of claim 1, wherein the composition is in a mold.

13. The method of claim 1, further comprising processing the composition to a desired shape after said compacting step, wherein said processing is selected from the group consisting of machining, turning, rolling, thread rolling, drilling, milling, sanding, punching, die cutting, blanking, broaching, and any combinations thereof.

14. The method of claim 1, further comprising inducing a conformational change in silk fibroin to a beta-sheet conformation, wherein said inducing a conformational change comprises solvent immersion, water annealing, water vapor annealing, sonication, pH reduction, exposure to an electric field, controlled slow drying, freeze-drying, compressing, heating, application of shear stress, and any combinations thereof.

* * * * *